United States Patent
Suda et al.

(10) Patent No.: US 9,605,248 B2
(45) Date of Patent: Mar. 28, 2017

(54) HYPERTHERMOSTABLE ENDOGLUCANASE BELONGING TO GH FAMILY 12

(71) Applicant: HONDA MOTOR CO., LTD., Minato-ku, Tokyo (JP)

(72) Inventors: Migiwa Suda, Kisarazu (JP); Jiro Okuma, Wako (JP); Yoshitsugu Hirose, Wako (JP); Asuka Yamaguchi, Tokyo (JP); Yasuhiro Kondo, Kawagoe (JP); Tomohiko Kato, Kisarazu (JP); Daisuke Shibata, Kisarazu (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 14/816,945

(22) Filed: Aug. 3, 2015

(65) Prior Publication Data

US 2016/0108385 A1    Apr. 21, 2016

(30) Foreign Application Priority Data

Aug. 4, 2014  (JP) ................. 2014-158651

(51) Int. Cl.
| | |
|---|---|
| C12P 7/04 | (2006.01) |
| C12N 9/24 | (2006.01) |
| C12N 9/42 | (2006.01) |
| C12P 19/02 | (2006.01) |
| C12P 19/14 | (2006.01) |

(52) U.S. Cl.
CPC ........... *C12N 9/2437* (2013.01); *C12N 9/248* (2013.01); *C12P 19/02* (2013.01); *C12P 19/14* (2013.01); *C12Y 302/01004* (2013.01); *C07K 2319/21* (2013.01); *C12Y 302/01008* (2013.01)

(58) Field of Classification Search
CPC .......... C12P 2203/00; C12P 7/04; C12N 9/24; C12Y 302/00
USPC ................... 435/183, 252.3, 320.1; 536/23.2
See application file for complete search history.

(56) References Cited

U.S. PATENT DOCUMENTS

| | | |
|---|---|---|
| 2002/0102699 A1 | 8/2002 | Wicher et al. |
| 2003/0054539 A1 | 3/2003 | Schulein et al. |
| 2003/0129723 A1 | 7/2003 | Ishikawa et al. |
| 2005/0070003 A1 | 3/2005 | Schulein et al. |
| 2005/0215450 A1 | 9/2005 | Outtrup et al. |
| 2008/0233175 A1 | 9/2008 | Steer et al. |

FOREIGN PATENT DOCUMENTS

| | | |
|---|---|---|
| JP | 2003-210812 A | 7/2003 |
| JP | 2014-027928 A | 2/2014 |
| WO | 9315186 A1 | 8/1993 |

OTHER PUBLICATIONS

Search Report Office Action dated Dec. 18, 2015 for corresponding European Patent Application No. 15 17 9521.8.
Kufner et al., "Construction of a Chimeric Thermoacidophilic Beta-Endoglucanase," BMC Biochemistry, 2013, pp. 1-9, 14:11, BioMed Central.
Wang et al., "Characterization of a Thermostable and Acidic-Tolerable Beta-Glucanase from Aerobic Fungi Trichoderma koningii ZJU-T," Journal of Food Science, 2007, pp. C452-C456, vol. 72, Nr. 9, Institute of Food Technologists.
Ando et al., "Hyperthermostable Endoglucanase from Pyrococcus horikoshii", Applied and Environmental Microbiology, Jan. 2002, vol. 68, No. 1, pp. 430-433.
Shi et al, Bioresource Technology 2013, vol. 142, pp. 338-344.
Zhang et al, Journal of Biotechnology, 1997, vol. 57, pp. 101-113.
Telke et al, "Engineering of Family-5 Glycoside Hydrolase (Cel5A) from an Uncultured Bacterium for Efficient Hydrolysis of Cellulosic Substrates", PLOS One, 2013, vol. 8, p. e65727.
Maurelli et al, Extremophiles, 2008, vol. 12, p. 689-700.
Quinlan et al., "Pyrobayes: an improved base caller for SNP discovery in pyrosequences", Nature Methods, 2008, vol. 5, No. 2, p. 179-181.
Hoff et al., "Orphelia: predicting genes in metagenomic sequencing reads", Nucleic Acids Research, 2009, vol. 37, Web Server issue : W101-W105.
Finn et al., "Pfam protein families database", Nucleic Acids Research Database, 2010, vol. 38, p. D211-222.
Durbin et al., 'The theory behind profile HMMs. Biological sequence analysis: probabilistic models of proteins and nucleic acids', 1998, Cambridge University Press.
Noguchi et al., "MetaGeneAnnotator: Detecting Species-Specific Patterns of Ribosomal Binding Site for Precise Gene Prediction in Anonymous Prokaryotic and Phage Genomes", DNA Research, 2008,15(6), pp. 387-396.

*Primary Examiner* — Maryam Monshipouri
(74) *Attorney, Agent, or Firm* — Carrier Blackman & Associates, P.C.; Joseph P. Carrier; Fulchand P. Shende

(57) ABSTRACT

A hyperthermostable endoglucanase including an endoglucanase catalytic domain, the endoglucanase catalytic domain including:

(A) a polypeptide including an amino acid sequence represented by SEQ ID NO: 3 or SEQ ID NO: 11;

(B) a polypeptide including an amino acid sequence in which at least one amino acid is deleted, substituted, or added in the amino acid sequence represented by SEQ ID NO: 3 or SEQ ID NO: 11, and having hydrolytic activity using carboxymethyl cellulose as a substrate at least under conditions of a temperature of 110° C. and a pH of 4.0; or (C) a polypeptide including an amino acid sequence having at least 70% sequence identity with the amino acid sequence represented by SEQ ID NO: 3 or SEQ ID NO: 11, and having hydrolytic activity using carboxymethyl cellulose as a substrate at least under conditions of a temperature of 110° C. and a pH of 4.0.

16 Claims, 8 Drawing Sheets

FIG. 1

```
AR15G-90         0 ------------------------------------------------------------ 0
I. aggregans     1 MAVSGLQIIVVILVIALLALGIYIVIGGPGTKTIVTETITYTETVPRTIIQQETKTITTI 60

AR15G-90         1 ------------------------------------------VTIITPSTTPQQLRAITLR 18
I. aggregans    61 IPTTIEGIVRETTTETQYTTVTSIATVTMTSILTSTVYQTVSQTIIYTTTTITSPMSIILE 120

AR15G-90        19 YPGNSS--SPVDLNSDGVYDVLLEINPWNMEKADGFQTIVVDLINGVIKVSSDLANVYPP 76
I. aggregans   121 YPKDLSTVKTLDINGDGISDVKVAINPWNMRSAQGYQKMIINLSTRSIKFISNLTNVSPA 180

AR15G-90        77 NWANGYPEIIIGRKPWTTYYYNGLGVEFPMRVRDARPFVISFYICVEHLDPSMNFNIAAD 136
I. aggregans   181 EWTNGYPEIYIGRKPWDYSYVNGFGVAFPMKISELKPFVVSFYICIDRLDPSMNFNIAAD 240

AR15G-90       137 AWIVRESIAMSLGMPPAKGDLEIMVWLFSQNLNPAGRKIGEEVVPISINGSVIEAVFEVW 196
I. aggregans   241 AWIVRESIARNAGASPSQGDIEIMVWLFNQNLQPAGSRIGEEILPIVINGTKYYKTFEVW 300

AR15G-90       197 RHDSVEWGGWQYIAFRPKMWGVRCGYIAYNPIDFVTAASKYAT-FDISDYYLLGWEIGTE 255
I. aggregans   301 KMNSVPWGGWDYIAFKPKDWSIRCGSVVYDPTQFVKALSKYTDGIDISNYYLLDWEIGTE 360

AR15G-90       256 WGTMTSNGLAKFSWFLKDLEIQPGKTLR                                 283
I. aggregans   361 WGSRTSNGIAIFEWTIRDFMAIPGIEIK                                 388
```

FIG. 10

```
AR15G-90B     1 ---MS--RKTAVIATALLTLMGFLAG----------------YPYGVSR-----VETMTT  37
AR15G-90      0 ------------------------------------------------------------   0
I. aggregans  1 MAVSGLQIIVILVIALALGIYIVIGPGTKTIVTETIYETVPRTIIQQETKIITI  60

AR15G-90B    38 VTI-------TATTFYSTITDITTVTIT--------------------PSTTPQQLRAITLR  73
AR15G-90      1 ------------------------------VTIT--------------PSTTPQQLRAITLR  18
I. aggregans 61 IPITIEGIVREDTETMTDMSIATVTMSILTSTVYQTIVTSQTIVTTITSPMSTITLE 120

AR15G-90B    74 YPGNSS---SPVDLNSDGVYVDLLEINPWMEKADGFQTIVDLINGVIKVSSDLANVYPP 131
AR15G-90     19 YPGNSS---SPVDLNSDGVYVDLLEINPWMEKADGFQTIVDLINGVIKVSSDLANVYPP  76
I. aggregans 121 YPKDLSTVKTLDINGDGISDVKVAINPMRSAQGYQKMIINLSTRSIKFISVLTIVSPA 180

AR15G-90B   132 NWANGYPEIIGRKPWTTYYYNGLGVEFPMRVRDARPFVISFYICVEHLDPSMNFNIAAD 191
AR15G-90     77 NWANGYPEIIGRKPWTTYYYNGLGVEFPMRVRDARPFVISFYICVEHLDPSMNFNIAAD 136
I. aggregans 181 EWTINGYPEIMGRKPWDYSMNGFGVAFPMKISELKPFWSFYICIDRLDPSMNFNIAAD 240

AR15G-90B   192 AMIVRESIAMSLGMPPAKGDLEIMWLFSQNLNPAGRKIGEEVVPISINGSVIEAVFEVW 251
AR15G-90    137 AMIVRESIAMSLGMPPAKGDLEIMWLFSQNLNPAGRKIGEEVVPISINGSVIEAVFEVW 196
I. aggregans 241 AMIVRESIARNAGASPSQGDIEIMWLFNQNLQPAGSRIGEEITLPMINGTKYKTFEVW 300

AR15G-90B   252 RHDSVEWGGMQYIAFRPKMWGVRCGYIAYNPIDFVTAASKYAT-FDISDYYLLGWEIGTE 310
AR15G-90    197 RHDSVEWGGMQYIAFRPKMWGVRCGYIAYNPIDFVTAASKYAT-FDISDYYLLGWEIGTE 255
I. aggregans 301 KMINSVPWGGWDYIAFKPKDWSIRCGSVVPPTQFVKALSKYTDGIDSNYYLDWEIGTE 360

AR15G-90B   311 WGTMTSNGLAKFSWFLKDLEIQPGKTLR 338
AR15G-90    256 WGTMTSNGLAKFSWFLKDLEIQPGKTLR 283
I. aggregans 361 WGSRTSNGIATFEMTIRDFMAIPGTEIK 388
```

HYPERTHERMOSTABLE ENDOGLUCANASE BELONGING TO GH FAMILY 12

TECHNICAL FIELD

The present invention relates to a hyperthermostable endoglucanase, a polynucleotide that encodes the aforementioned hyperthermostable endoglucanase, an expression vector for expressing the aforementioned hyperthermostable endoglucanase, a transformant incorporated with the aforementioned expression vector, and a method for producing a lignocellulose degradation product using the aforementioned hyperthermostable endoglucanase.

Priority is claimed on Japanese Patent Application No. 2014-158651, filed Aug. 4, 2014, the content of which is incorporated herein by reference.

BACKGROUND ART

In recent years, the development of alternative energy to oil is a very important issue, because of environmental problems, such as global warming and aerial pollution, in addition to the concern related to transportation energy supply. Plant biomass is the most abundant renewable energy source on earth, which is expected to serve as an alternative source to petroleum. Lignocellulose is the main component of plant biomass and is composed of polysaccharides such as celluloses and hemicelluloses (including xylan, arabinan and mannan), lignin and other pectins. These polysaccharides are hydrolyzed into monosaccharides such as glucose and xylose by a variety of glycoside hydrolases, and are used as a biofuel or a raw material of chemical products.

Lignocellulose having a complex structure is persistent, and is difficult to degrade or hydrolyze with a single enzyme. For this reason, the hydrolysis of cellulose among the polysaccharides generally requires three types of enzymes: an endoglucanase (endo-1,4-β-D-glucanase, EC 3.2.1.4), an exo-type cellobiohydrolase (1,4-β-cellobiosidase or cellobiohydrolase, EC 3.2.1.91, EC 3.2.1.176), and a β-glucosidase (EC 3.2.1.21) that are glycoside hydrolases. On the other hand, hemicellulose contains xylan, arabinan, mannan and the like, and the composition thereof depends on the type of the plants. For example, xylan is a major constituent in broad-leaved trees, herbaceous plants and the like. For the hydrolysis of xylan, it is thought that xylanase (endo-1,4-β-xylanase, EC 3.2.1.8) and β-xylosidase (EC 3.2.1.37) are required.

In the conventional lignocellulose to ethanol conversion process, high-solid loading up to 30-60% in initial substrate concentration has been attempted for the purpose of higher energy efficiency and less water usage. The enzymatic hydrolysis of lignocellulose by such high-solid loading processes results in the high viscosity of the hydrolyzed biomass solution so that the hydrolysis of lignocellulose hardly proceeds. Therefore, for example, by carrying out the enzymatic hydrolysis process at a high temperature of 80° C. or higher using a thermostable enzyme, in addition to an increase in the hydrolysis reaction rate, since the viscosity of the hydrolyzed biomass solution also reduces, the shortening of the hydrolysis reaction time and the reduction of the amount of enzyme are expected to be achieved. For this reason, for various glycoside hydrolases, development of enzymes that are more excellent in terms of thermostability has been desired.

Many thermostable glycoside hydrolases have been obtained by isolating and identifying the thermophilic microorganisms that live in a high temperature environment, cloning the genes from these cultured and isolated microorganisms and determining the DNA sequence thereof, followed by the expression thereof using *Escherichia coli*, filamentous fungi and the like. For the purpose of lignocellulose degradation, use as a processing agent of cellulose fibers, and pulp and paper processing, numerous thermostable enzymes that can be used for lignocellulose hydrolysis treatment at a high temperature, especially endoglucanases necessary for the hydrolysis of cellulose, have been isolated to date from thermophilic bacteria, filamentous fungi, archaea and the like (for example, see Patent Documents 1 to 4, and Non-Patent Documents 1 and 2). In addition, attempts have also been made to further improve the specific activity and the heat resistance, for example, by using the mutants of a host organism or partially modifying the amino acid sequences of these enzymes (for example, see Non-Patent Documents 3 and 4). However, most of these enzymes have an optimum temperature of 60 to 80° C., and a further increase in the degree of heat resistance has been desired. On the other hand, hyperthermostable endoglucanases having an optimum temperature of more than 90° C. have been reported (for example, see Patent Documents 5 to 7, and Non-Patent Documents 1 and 5). According to Non-Patent Document 5, an endoglucanase of *Sulfolobus solfataricus* having an optimum temperature of 95° C., has been reported, although the specific activity thereof is 5.5 U/mg protein at 90° C., which is not high. The above enzyme also has xylanase activity, although the specific activity of xylanase is 4.0 U/mg protein 90° C., which is also low.

PRIOR ART DOCUMENTS

Patent Documents

[Patent Document 1] United States Patent Application Publication No. 2003/0054539
[Patent Document 2] United States Patent Application Publication No. 2005/0070003
[Patent Document 3] United States Patent Application Publication No. 2003/0129723
[Patent Document 4] United States Patent Application Publication No. 2005/0215450
[Patent Document 5] Japanese Unexamined Patent Application, First Publication No. 2003-210182
[Patent Document 6] Japanese Unexamined Patent Application, First Publication No. 2014-27928
[Patent Document 7] United States Patent Application Publication No. 2002/0102699

Non-Patent Documents

[Non-Patent Document 1] Ando et al., Applied and Environmental Microbiology, 2002, vol. 68, p. 430-433.
[Non-Patent Document 2] Shi et al., Bioresource Technology 2013, vol. 142, p 338-344.
[Non-Patent Document 3] Zhang et al., Journal of Biotechnology, 1997, vol. 57, p. 101-113.
[Non-Patent Document 4] Telke et al., PloS One, 2013, vol. 8, p. e65727.
[Non-Patent Document 5] Maurelli et al., Extremophiles, 2008, vol. 12, p. 689-700.

SUMMARY OF THE INVENTION

Problems to be Solved by the Invention

It is an object of the present invention to provide a novel hyperthermostable endoglucanase which exhibits hydrolytic activity using carboxymethyl cellulose (hereinafter, may be abbreviated as CMC) as a substrate at least under conditions of a temperature of 110° C. and a pH of 4.0, a polynucleotide that encodes the aforementioned hyperthermostable endoglucanase, an expression vector for expressing the aforementioned hyperthermostable endoglucanase, a transformant incorporated with the aforementioned expression vector, and a method for producing a lignocellulose degradation product using the aforementioned hyperthermostable endoglucanase.

Means for Solving the Problem

In order to solve the above-mentioned problems, the inventors of the present invention have successfully obtained hyperthermostable endoglucanases having novel amino acid sequences by extracting DNA directly from hot spring high temperature soils and conducting large-scale metagenome sequencing of hardly culturable microbiota. This has led to the completion of the present invention.

That is, as a hyperthermostable endoglucanase, a polynucleotide, an expression vector, a transformant, a method for producing a hyperthermostable endoglucanase, a glycoside hydrolase mixture and a method for producing a lignocellulose degradation product according to the present invention, the following aspects [1] to [10] can be mentioned.

[1] A hyperthermostable endoglucanase including an endoglucanase catalytic domain, the endoglucanase catalytic domain including: (A) a polypeptide including an amino acid sequence represented by SEQ ID NO: 3 or SEQ ID NO: 11;

(B) a polypeptide including an amino acid sequence in which at least one amino acid is deleted, substituted, or added in the amino acid sequence represented by SEQ ID NO: 3 or SEQ ID NO: 11, and having hydrolytic activity using carboxymethyl cellulose as a substrate at least under conditions of a temperature of 110° C. and a pH of 4.0; or (C) a polypeptide including an amino acid sequence having at least 70% sequence identity with the amino acid sequence represented by SEQ ID NO: 3 or SEQ ID NO: 11, and having hydrolytic activity using carboxymethyl cellulose as a substrate at least under conditions of a temperature of 110° C. and a pH of 4.0.

[2] The hyperthermostable endoglucanase according to the aforementioned aspect [1], wherein the aforementioned endoglucanase catalytic domain also has xylanase activity under conditions of a temperature of 110° C. and a pH of 7.0.

[3] A polynucleotide including a region that encodes an endoglucanase catalytic domain which includes: (a) a nucleotide sequence that encodes a polypeptide including an amino acid sequence represented by SEQ ID NO: 3 or SEQ ID NO: 11;

(b) a nucleotide sequence that encodes a polypeptide including an amino acid sequence in which at least one amino acid is deleted, substituted, or added in the amino acid sequence represented by SEQ ID NO: 3 or SEQ ID NO: 11, and having hydrolytic activity using carboxymethyl cellulose as a substrate at least under conditions of a temperature of 110° C. and a pH of 4.0;

(c) a nucleotide sequence that encodes a polypeptide including an amino acid sequence having at least 70% sequence identity with the amino acid sequence represented by SEQ ID NO: 3 or SEQ ID NO: 11, and having hydrolytic activity using carboxymethyl cellulose as a substrate at least under conditions of a temperature of 110° C. and a pH of 4.0;

(d) a nucleotide sequence having at least 70% sequence identity with a nucleotide sequence represented by SEQ ID NO: 4 or SEQ ID NO: 12, and encoding a polypeptide having hydrolytic activity using carboxymethyl cellulose as a substrate at least under conditions of a temperature of 110° C. and a pH of 4.0; or (e) a nucleotide sequence of a polynucleotide which hybridizes with a polynucleotide including a nucleotide sequence represented by SEQ ID NO: 4 or SEQ ID NO: 12 under a stringent condition, and being a nucleotide sequence that encodes a polypeptide having hydrolytic activity using carboxymethyl cellulose as a substrate at least under conditions of a temperature of 110° C. and a pH of 4.0.

[4] The polynucleotide according to the aforementioned aspect [3], wherein the aforementioned polypeptide also has xylanase activity under conditions of a temperature of 110° C. and a pH of 7.0.

[5] An expression vector, which is incorporated with the polynucleotide according to the aforementioned aspect [3] or [4], and which is able to express a polypeptide having endoglucanase activity in a host cell.

[6] A transformant, which is introduced with the expression vector according to the aforementioned aspect [5].

[7] The transformant according to the aforementioned aspect [6], which is a eukaryotic microbe.

[8] A method for producing a hyperthermostable endoglucanase, the method including a step of producing a hyperthermostable endoglucanase in the transformant according to the aforementioned aspect [6] or [7].

[9] A glycoside hydrolase mixture, including the hyperthermostable endoglucanase according to the aforementioned aspect [1] or [2], a hyperthermostable endoglucanase encoded by the polynucleotide according to the aforementioned aspect [3] or [4], or a hyperthermostable endoglucanase produced by the method for producing a hyperthermostable endoglucanase according to the aforementioned aspect [8], and at least one or more types of other glycoside hydrolases.

[10] A method for producing a lignocellulose degradation product, the method including a step of producing a lignocellulose degradation product by bringing a material composed of lignocellulose including cellulose into contact with the hyperthermostable endoglucanase according to the aforementioned aspect [1] or [2], a hyperthermostable endoglucanase encoded by the polynucleotide according to the aforementioned aspect [3] or [4], the transformant according to the aforementioned aspect [6] or [7], a hyperthermostable endoglucanase produced by the method for producing a hyperthermostable endoglucanase according to the aforementioned aspect [8], or the glycoside hydrolase mixture according to the aforementioned aspect [9].

Effects of the Invention

The hyperthermostable endoglucanase according to the present invention has hydrolytic activity using CMC as a substrate at least under conditions of a temperature of 110°

C. and a pH of 4.0. For this reason, the aforementioned hyperthermostable endoglucanase is suitable for a hydrolysis process of materials composed of lignocellulose including cellulose in high temperature conditions.

In addition, the polynucleotide, the expression vector incorporated with the aforementioned polynucleotide and the transformant introduced with the aforementioned expression vector according to the present invention are suitably used for the production of the hyperthermostable endoglucanase according to the present invention.

BRIEF DESCRIPTION OF THE DRAWINGS

FIG. 1 is an alignment representation of the amino acid sequence (SEQ ID NO: 1) of a polypeptide (hereinafter, may be referred to as AR15G-90) encoded by an open reading frame AR15G-90 and the amino acid sequence of a glycoside hydrolase family 12 (SEQ ID NO: 8) of *Ignisphaera aggregans* DISM 17230.

FIG. 10 is an alignment representation of the amino acid sequence (SEQ ID NO: 1) of a polypeptide (AR15G-90) encoded by the open reading frame AR15G-90, the amino acid sequence (SEQ ID NO: 9) of a polypeptide (hereinafter, may be referred to as AR15G-908) encoded by an open reading frame AR15G-90B, and the amino acid sequence of a glycoside hydrolase family 12 (SEQ ID NO: 8) of *Ignisphaera aggregans* DSM17230.

DESCRIPTION OF THE EMBODIMENT

[Hyperthermostable Endoglucanase]

Figure 2:
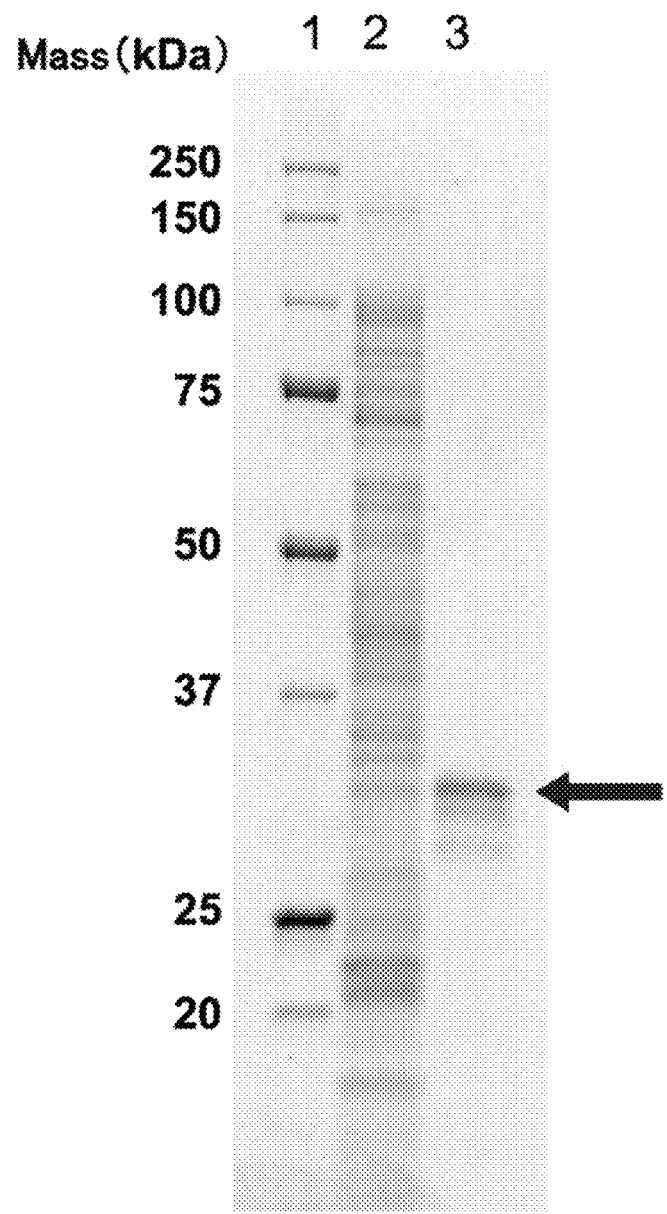
FIG. 2 is a diagram showing the results of SDS-PAGE analysis of the AR15G-90-3 protein obtained by expressing the AR15G-90-3 gene in *E. coli* in Example 1.

Many microorganisms including filamentous fungi, bacteria and archaea are difficult to culture, and about 99% of the microbes living in the microbial environments such as soil are said to be unknown microbes. In particular, the culturing of microorganisms living in a high temperature environment is extremely difficult, and it is thought that merely 0.1% or less of the microorganisms living in soils have been isolated and cultured with the currently available microbial culturing techniques. This difficulty to culture such microorganisms living in high temperature soils is one factor to hinder the development of thermostable enzymes.

In recent years, because of the development of the next generation giga sequencer enabling large amount sequencing of giga base pairs, it has become possible to conduct the whole genome sequencing of the microbiota contained in soil and the like. Using this analysis technology, the metagenomic analysis method has been proposed in which the genome DNA of a microbial group is prepared from an environmental sample such as soil, the genomes of the group having nonuniform and miscellaneous genomic organizations are directly and comprehensively sequenced, and the sequenced data are assembled by a parallel computer, so as to thereby reconstruct the genomic sequences of the microbiota. This has contributed to the rapid progress in the genome sequencing of hardly culturable microorganisms.

As shown in Example 1 described later, the inventors of the present invention extracted the genomic DNA (metagenomic DNA) of the microbial groups collected from high temperature hot spring soils (for example, hot spring water of 58 to 78° C. that contained soil, mud, microbial mats, biofilms and the like may be mentioned), and conducted shotgun sequencing and annotation of the metagenomic DNA. By so doing, open reading frames (ORFs) encoding the amino acid sequences similar to known endoglucanase enzymes (for example, amino acid sequences having 20% or higher sequence identity and the Expectation value (E-value) of less than $1e^{-20}$) were obtained. Of these ORFs, primers were designed based on the nucleotide sequence information of 106 ORFs in which the presence of endoglucanase catalytic domain could be verified, and gene candidates were cloned from the metagenomic DNA of the high temperature hot spring soils by the PCR method. The PCR-cloned DNAs were incorporated into *E. coli*, and proteins encoded by the aforementioned nucleotide sequences were expressed. These were subjected to functional screenings by assays on the CMC hydrolysis activity. In the end, a hyperthermostable endoglucanase having endoglucanase activity (hereinafter, may be referred to as "AR15G-90-3") was obtained from these ORFs. The amino acid sequence of AR15G-90-3 and the nucleotide sequence encoding the amino acid sequence of AR15G-90-3 are represented by SEQ ID NO: 3 and SEQ ID NO: 4, respectively.

It should be noted that AR15G-90-3 is a partial protein in which the N-terminus is missing, and as shown in Example 2 described later. AR15G-90B-15 is a full-length protein of AR15G-90-3. The amino acid sequence of AR15G-90B-15 and the nucleotide sequence encoding the amino acid sequence of AR15G-90B-15 are represented by SEQ ID NO: 11 and SEQ ID NO: 12, respectively.

As shown in Example 1 <9> described later. AR15G-90-3 exhibited particularly high hydrolysis activity for lichenan, also exhibited high hydrolysis activity for CMC, phosphoric acid swollen Avicel (hereinafter, may be abbreviated as PSA) which is a non-crystalline cellulose and xylan, and also exhibited hydrolysis activity for Avicel which is a crystalline cellulose, laminarin, and p-nitrophenyl-β-D-cellobioside (hereinafter, may be abbreviated as PNPC). On the other hand, it exhibits almost no degradation activity for p-nitrophenyl-β-D-glucopyranoside (hereinafter, may be abbreviated as PNPG) and p-nitrophenyl-β-D-xylopyranoside (hereinafter, may be abbreviated as PNPX).

In other words, one aspect of AR15G-90-3 is a hyperthermostable endoglucanase exhibiting high substrate specificity for compounds having β-1,4 bonds (for example, CMC, PSA, Avicel, PNPC, and the like) and compounds having β-1,3 bonds and β-1,4 bonds (for example, lichenan, and the like), and also having xylanase activity.

The amino acid sequence of AR15G-90-3 was searched in publicly known amino acid sequence databases, resulting that the amino acid sequence showing the highest sequence identity was of a glycoside hydrolase family 12 (Genbank: ADM27292.1) (SEQ ID NO: 8) of *Ignisphaera aggregans* DSM17230 in the phylum Crenarchaeota, with the sequence identity (homology) of 56% in full length and 64% for the GH12 catalytic domain. From the substrate specificity and the sequence identity of the amino acid sequence with those of the already known proteins, it is clear that AR15G-90-3 is a novel endoglucanase belonging to the GH12 family.

AR15G-90-3 has hydrolytic activity using CMC as a substrate at least under conditions of a temperature of 110° C. and a pH of 4.0. Actually, as shown in Example 1 <10> and <1> described later, AR15G-90-3 exhibits endoglucanase activity within a wide temperature range of 60 to 160° C. and within a wide pH range of 3 to 8, exhibits strong endoglucanase activity within a temperature range of 80 to 120° C. and a pH of 3 to 8, and exhibits very strong endoglucanase activity within a temperature range of 90 to 110° C. and a pH of 4 to 6.

More specifically, the CMC hydrolysis activity of AR15G-90-3 at a pH of 4.0 using CMC as a substrate tends to increase as the temperature increases within a range from 60 to 90° C., tends to be high and stable within a range from 90 to 120° C., and tends to decrease gradually at a temperature of 120° C. or higher.

Further, in addition to the endoglucanase activity, AR15G-90-3 also has xylanase activity under conditions of a temperature of 110° C. and a pH of 7.0. Actually, as shown in Example 1 <12> and <13> described later, AR15G-90-3 exhibits xylanase activity within a wide temperature range of 40 to 140° C. and within a wide pH range of 5 to 10, exhibits strong xylanase activity within a temperature range of 80 to 120° C. and a pH of 6 to 9.5, and exhibits very strong xylanase activity within a temperature range of 90 to 115° C. and a pH of 6.5 to 9.

More specifically, the xylanase activity of AR15G-90-3 at a pH of 7.0 using xylan as a substrate tends to increase as the temperature increases within a range from 40 to 110° C., and tends to decrease rapidly when the temperature exceeds 110° C.

It should be noted that in the present invention and the description of this application, the expression "having activity" or "exhibiting activity" refers to an action on at least one substrate and means that a significant difference occurs in the hydrolyzed amount of reducing ends of the substrate or the color reaction as compared to the negative control.

Therefore, the expression "having endoglucanase activity" refers to an action on at least one substrate selected from the group consisting of compounds having β-1,4 bonds (for example, CMC, PSA, Avicel, PNPC, and the like) and compounds having β-1,3 bonds and β-1,4 bonds (for example, lichenan, and the like), and means that a significant difference occurs in the hydrolyzed amount of reducing ends of the substrate or the color reaction as compared to the negative control.

The expression "having xylanase activity" refers to an action on at least xylan and means that a significant difference occurs in the hydrolyzed amount of reducing ends of xylan or the color reaction as compared to the negative control.

Generally, in a protein having some kind of bioactivity, one or two or more amino acids can be deleted, substituted, or added, without deteriorating the bioactivity. In other words, also in AR15G-90-3, one or two or more amino acids can be deleted, substituted, or added, without causing loss of glycoside hydrolysis activity.

That is, the hyperthermostable endoglucanase according to the present invention is a hyperthermostable glycoside hydrolase having an endoglucanase catalytic domain which includes any one of the following (A) to (C):

(A) a polypeptide including an amino acid sequence represented by SEQ ID NO: 3 or SEQ ID NO: 11 (that is, AR15G-90-3);

(B) a polypeptide including an amino acid sequence in which at least one amino acid is deleted, substituted, or added in the amino acid sequence represented by SEQ ID NO: 3 or SEQ ID NO: 11, as well as having hydrolytic activity using CMC as a substrate at least under conditions of a temperature of 110° C. and a pH of 4.0; or (C) a polypeptide including an amino acid sequence having at least 70% sequence identity with the amino acid sequence represented by SEQ ID NO: 3 or SEQ ID NO: 11, as well as having hydrolytic activity using CMC as a substrate at least under conditions of a temperature of 110° C. and a pH of 4.0.

In the present invention and the description of this application, a "polypeptide in which an amino acid is deleted" means that a portion of the amino acids which constitute the polypeptide is missing (that is, removed).

In the present invention and the description of this application, a "polypeptide in which an amino acid is substituted" means that an amino acid which constitutes the polypeptide is replaced with a different amino acid.

In the present invention and the description of this application, a "polypeptide in which an amino acid is added" means that a new amino acid is inserted within the polypeptide.

In the aforementioned polypeptide of (B), the number of amino acids to be deleted, substituted, or added in the amino acid sequence represented by SEQ ID NO: 3 or SEQ ID NO: 11 is preferably from 1 to 20, more preferably from 1 to 10, and still more preferably from 1 to 5.

In the aforementioned polypeptide of (C), the sequence identity with the amino acid sequence represented by SEQ ID NO: 3 or SEQ ID NO: 11 is not particularly limited as long as it is 70% or greater but less than 100%, although it is preferable to be 75% or greater but less than 100%, more preferably 80% or greater but less than 100%, still more preferably 85% or greater but less than 100%, still more preferably 90% or greater but less than 100%, and particularly preferably 95% or greater but less than 100%.

It should be noted that the sequence identity (homology) between a pair of amino acid sequences is obtained such that: two amino acid sequences are juxtaposed while having gaps in some parts accounting for insertion and deletion so that the largest numbers of corresponding amino acids can be matched, and the sequence identity is deemed to be the proportion of the matched amino acids relative to the whole amino acid sequences excluding the gaps, in the resulting alignment. The sequence identity between a pair of amino acid sequences can be obtained by using a variety of homology search software publicly known in the art. The sequence identity value between amino acid sequences in the present invention is obtained by calculation on the basis of an alignment obtained from a publicly known homology search software BLASTP.

The aforementioned polypeptides of (B) and (C) may be those that are artificially designed, or may also be homologues of AR15G-90-3 and the like, or partial proteins thereof.

The aforementioned polypeptides of (A) to (C) may be respectively synthesized in a chemical manner based on the amino acid sequence, or may also be produced by a protein expression system using the polynucleotide according to the present invention that will be described later. In addition, the aforementioned polypeptides of (B) and (C) can also be respectively synthesized artificially based on a polypeptide including the amino acid sequence represented by SEQ ID NO: 3 or SEQ ID NO: 11, by using a genetic recombination technique to introduce amino acid mutation(s).

The aforementioned polypeptides of (A) to (C) have hydrolysis activities using CMC as a substrate at least under conditions of a temperature of 110° C. and a pH of 4.0. For this reason, a hyperthermostable endoglucanase can be obtained by having any one of the aforementioned polypeptides of (A) to (C) as the endoglucanase catalytic domain.

The hyperthermostable endoglucanase according to the present invention uses at least one selected from the group consisting of a compound having a β-1,3 bond and a β-1,4 bond, a compound having a β-1,4 bond, and xylan as a substrate.

Such compounds having a β-1,3 bond and a β-1,4 bond can be exemplified by lichenan, β-glucan, and the like. Such compounds having a β-1,4 bond can be exemplified by crystalline celluloses such as Avicel, bacterial microcrystalline cellulose (BMCC), and filter paper, CMC, PSA, cellobiose, and the like.

The hyperthermostable endoglucanase according to the present invention preferably uses, in addition to CMC and xylan, at least one member selected from the group consisting of lichenan, β-glucans, PSA, Avicel, PNPC, and xyloglucan as a substrate; more preferably uses, in addition to CMC and xylan, at least one member selected from the group consisting of lichenan, PSA, and xyloglucan as a substrate; and still more preferably uses CMC, xylan and lichenan as substrates.

The hyperthermostable endoglucanase according to the present invention may also use, in addition to the above substrates, another type of glucan as a substrate. Examples of those that can also be used as a substrate by the hyperthermostable endoglucanase according to the present invention include PNPX, p-nitrophenyl-β-D-glucopyranoside, p-nitrophenyl-α-L-arabinofuranoside, p-nitrophenyl-α-L-arabinopyranoside, p-nitrophenyl-β-L-arabinopyranoside, p-nitrophenyl-β-D-mannopyranoside, p-nitrophenyl-α-D-galactopyranoside, p-nitrophenyl-β-D-galactopyranoside; a glucan composed of β-1,3 bonds and β-1,6 bonds such as laminarin; a glucan composed of β-1,3 bonds; a glucan composed of β-1,6 bonds and an oligosaccharide composed of β-1,6 bonds such as gentiobiose.

The hyperthermostable endoglucanase according to the present invention preferably exhibits CMC hydrolysis activity at least under conditions of a pH of 4.0 within a temperature range from 90 to 110° C., more preferably within a temperature range from 80 to 120° C., and still more preferably within a wide temperature range from 60 to 160° C. The optimum temperature for the CMC hydrolysis activity of the hyperthermostable endoglucanase according to the present invention is preferably within the range from 90 to 120° C. under a condition of a pH of 4.0.

Although the optimum pH for the endoglucanase activity of the hyperthermostable endoglucanase according to the present invention varies depending on the reaction temperature and the substrate, it is within a pH range from 4.0 to 5.0. For example, the optimum pH at 70° C. in the case of using CMC as a substrate is 4.4. The hyperthermostable endoglucanase according to the present invention preferably exhibits endoglucanase activity at least within a pH range from 4 to 6, and more preferably exhibits endoglucanase activity within a pH range from 3 to 8.

The hyperthermostable endoglucanase according to the present invention preferably further exhibits xylanase activity at least under a condition of a pH of 7.0 within a temperature range from 90 to 115° C., more preferably within a temperature range from 80 to 120° C., and still more preferably within a wide temperature range from 40 to 140° C. The optimum temperature for the xylanase activity of the hyperthermostable endoglucanase according to the present invention is preferably within the range from 90 to 120° C. under a condition of a pH of 7.0, and more preferably within the range from 100 to 115° C.

Although the optimum pH for the xylanase activity of the hyperthermostable endoglucanase according to the present invention varies depending on the reaction temperature and the like, it is within a pH range from 6.5 to 9.0, and is preferably within a pH range from 7.5 to 8.5. The hyperthermostable endoglucanase according to the present invention preferably exhibits xylanase activity at least within a pH range from 6.5 to 9.0, and more preferably exhibits xylanase activity within a pH range from 5 to 10.

The hyperthermostable endoglucanase according to the present invention may also have another type of glycoside hydrolysis activity other than the endoglucanase activity and the xylanase activity. Such another type of glycoside hydrolysis activity can be exemplified by β-xylosidase activity, β-glucosidase activity, cellobiohydrolase activity, or the like.

The hyperthermostable endoglucanase according to the present invention may be an enzyme solely consisting of an endoglucanase catalytic domain which includes any one of the aforementioned polypeptides of (A) to (C), or may further include other domains. Examples of other domains include a domain present in the known glycoside hydrolases other than the enzyme catalytic domain. For example, the hyperthermostable endoglucanase according to the present invention also includes enzymes obtained by substituting an enzyme catalytic domain in a publicly known glycoside hydrolase with the aforementioned polypeptides of (A) to (C).

If the hyperthermostable endoglucanase according to the present invention includes a domain other than the endoglucanase catalytic domain, it is also preferable to include a cellulose-binding module. The cellulose-binding module may be either on the upstream (N-end side) or the downstream (C-end side) of the endoglucanase catalytic domain. In addition, the cellulose-binding module and the endoglucanase catalytic domain may be directly linked, or linked via a linker domain of an appropriate length. The hyperthermostable endoglucanase according to the present invention is preferably such that the cellulose-binding module is present on the upstream or the downstream of the endoglucanase catalytic domain via a linker domain, more preferably such that the cellulose-binding module is present on the upstream of the endoglucanase catalytic domain via a linker domain.

The cellulose-binding module contained in the hyperthermostable endoglucanase according to the present invention may suffice if it is a domain having an ability to bind to cellulose, for example, a domain having an ability to bind to PSA or a crystalline Avicel. The amino acid sequence thereof is not particularly limited. As the cellulose-binding module, for example, a cellulose-binding module of an already known protein or appropriately modified product thereof may be used. In addition, if the hyperthermostable endoglucanase according to the present invention has an endoglucanase catalytic domain and a cellulose-binding module, it is preferable that these are linked via a linker sequence. The amino acid sequence, the length, and the like, of the linker sequence are not particularly limited.

In addition, the hyperthermostable endoglucanase according to the present invention may also have a signal peptide enabling to transport it to a specific region to effect localization within a cell, or a signal peptide to effect extracellular secretion, at the N end or the C end. Such a signal peptide can be exemplified by an apoplastic transport signal peptide, an endoplasmic reticulum retention signal peptide, a nuclear transport signal peptide, a secretory signal peptide, or the like. The endoplasmic reticulum retention signal peptide can be exemplified by, for example, a signal peptide including a HDEL amino acid sequence, or the like. In those cases where the hyperthermostable endoglucanase according to the present invention has a signal peptide at the N end or the C end, the hyperthermostable endoglucanase expressed in a transformant can be secreted outside the cell, or can be localized in the intracellular endoplasmic reticulum, or the like.

In addition, the hyperthermostable endoglucanase according to the present invention may also be added with, for example, various types of tags at the N end or the C end, so as to enable easy and convenient purification in a case of the production using an expression system. Regarding such a tag, for example, it is possible to use a tag for usual use in the expression or purification of a recombinant protein, such as a His tag, a HA (hemagglutinin) tag, a Myc tag, and a Flag tag.

[Polynucleotide that Encodes Hyperthermostable Endoglucanase]

The polynucleotide according to the present invention encodes the hyperthermostable endoglucanase according to the present invention. The aforementioned hyperthermostable endoglucanase can be produced by using the expression system of a host made by introducing an expression vector incorporated with the polynucleotide into the host.

More specifically, the polynucleotide according to the present invention is a polynucleotide having a region that encodes an endoglucanase catalytic domain which includes any one of the following nucleotide sequences (a) to (e).

(a) a nucleotide sequence that encodes a polypeptide including an amino acid sequence represented by SEQ ID NO: 3 or SEQ ID NO: 11;
(b) a nucleotide sequence that encodes a polypeptide including an amino acid sequence in which at least one amino acid is deleted, substituted, or added in the amino acid sequence represented by SEQ ID NO: 3 or SEQ ID NO: 11, as well as having hydrolytic activity using CMC as a substrate at least under conditions of a temperature of 110° C. and a pH of 4.0;
(c) a nucleotide sequence that encodes a polypeptide including an amino acid sequence having at least 70% sequence identity with the amino acid sequence represented by SEQ ID NO: 3 or SEQ ID NO: 11, as well as having hydrolytic activity using CMC as a substrate at least under conditions of a temperature of 110° C. and a pH of 4.0;
(d) a nucleotide sequence having at least 70% sequence identity with a nucleotide sequence represented by SEQ ID NO: 4 or SEQ ID NO: 12, as well as encoding a polypeptide having hydrolytic activity using CMC as a substrate at least under conditions of a temperature of 110° C. and a pH of 4.0; or
(e) a nucleotide sequence of a polynucleotide which hybridizes with a polynucleotide including a nucleotide sequence represented by SEQ ID NO: 4 or SEQ ID NO: 12 under a stringent condition, as well as being a nucleotide sequence that encodes a polypeptide having hydrolytic activity using CMC as a substrate at least under conditions of a temperature of 110° C. and a pH of 4.0.

It should be noted that in the present invention and the description of this application, a "polynucleotide in which a nucleotide is deleted" means that a portion of the nucleotides which constitute the polynucleotide is missing (that is, removed).

In the present invention and the description of this application, a "polynucleotide in which a nucleotide is substituted" means that a nucleotide which constitutes the polynucleotide is replaced with a different nucleotide.

In the present invention and the description of this application, a "polynucleotide in which a nucleotide is added" means that a new nucleotide is inserted within the polynucleotide.

In the present invention and the description of this application, the term "under a stringent condition" can be exemplified by the method described in Molecular Cloning—A Laboratory Manual Third Edition (Sambrook et al., Cold Spring Harbor Laboratory Press). The example thereof includes a condition in which hybridization is performed by incubation in a hybridization butter including 6×SSC (composition of 20×SSC: 3M sodium chloride, 0.3M citric acid solution, and pH7.0), 5×Denhardt's solution (composition of 100×Denhardt's solution: 2 mass % bovine serum albumin, 2 mass % Ficoll, 2 mass % polyvinylpyrrolidone), 0.5 mass % SDS, 0.1 mg/mL salmon sperm DNA, and 50% formamide, at a temperature of 42 to 70° C. for several hours to overnight. The washing buffer for use in the washing after the incubation is preferably 1×SSC solution containing 0.1 mass % SDS, and more preferably 0.1×SSC solution containing 0.1 mass % SDS.

In the aforementioned nucleotide sequences of (a) to (e), it is preferable to select a degenerate codon having high frequency of usage in the host. For example, the aforementioned nucleotide sequence of (a) may be either the nucleotide sequence represented by SEQ ID NO: 4 or SEQ ID NO: 12, or a nucleotide sequence altered to have a codon having high frequency of usage in the host without changing the amino acid sequence to be encoded by the nucleotide sequence represented by SEQ ID NO: 4 or SEQ ID NO: 12. Note that, these codons can be altered by a publicly known gene sequence modification technique or artificial gene synthesis.

The polynucleotide including the nucleotide sequence represented by SEQ ID NO: 4 or SEQ ID NO: 12 may be synthesized in a chemical manner based on the nucleotide sequence information, or may be obtained as a full length of a gene that encodes AR15G-90-3 (may be referred to as "AR15G-90-3 gene" or "gene clone AR15G-90-3") or a gene that encodes AR15G-90B-15 (may be referred to as "AR15G-90B-15 gene" or "gene clone AR15G-90B-15"), or a partial region thereof including the endoglucanase catalytic domain (in the case of the AR15G-90-3 gene, a region encoding a partial region composed of 171 amino acid residues from glycine (G) at position 101 to leucine (L) at position 271 in SEQ ID NO: 3) from the natural world by using a genetic recombination technique. The full length of the AR15G-90-3 gene or AR15G-90B-15 gene or the partial region thereof can be obtained by, for example, collecting a sample containing microorganisms from the natural world, and conducting PCR using the genomic DNA recovered from the sample as a template, with a forward primer and a reverse primer designed on the basis of the nucleotide sequence represented by SEQ ID NO: 4 or SEQ ID NO: 12 by a conventional method. The cDNA synthesized by a reverse transcription reaction using mRNA recovered from the sample as a template may also be used as a template. Note that, it is preferable that the sample for recovering the nucleic acid serving as a template is a sample collected from a high temperature environment such as hot spring soil.

In the aforementioned nucleotide sequence of (d), the sequence identity with the nucleotide sequence represented by SEQ ID NO: 4 or SEQ ID NO: 12 is not particularly limited as long as it is 70% or greater but less than 100%, although it is preferable to be 75% or greater but less than 100%, more preferably 80% or greater but less than 100%, still more preferably 85% or greater but less than 100%, still more preferably 90% or greater but less than 100%, and particularly preferably 95% or greater but less than 100%.

Note that, the sequence identity (homology) between a pair of nucleotide sequences is obtained such that: two nucleotide sequences are juxtaposed while having gaps in some parts accounting for insertion and deletion so that the largest numbers of corresponding nucleotides can be matched, and the sequence identity is deemed to be the proportion of the matched nucleotides relative to the whole nucleotide sequences excluding gaps, in the resulting alignment. The sequence identity between a pair of nucleotide sequences can be obtained by using a variety of homology search software publicly known in the art. The sequence identity value between nucleotide sequences in the present invention is obtained by calculation on the basis of an alignment obtained from a publicly known homology search software BLASTN.

For example, the polynucleotide including the aforementioned nucleotide sequence of (b), (c), or (d) can be respectively synthesized artificially by deleting, substituting, or adding one or two or more nucleotides in a polynucleotide including the nucleotide sequence represented by SEQ ID NO: 4 or SEQ ID NO: 12. In addition, the aforementioned nucleotide sequence of (b), (c), or (d) may also be a full length sequence of a homologous gene of the AR15G-90-3 gene (or the AR15G-90B-15 gene) or a partial sequence thereof. The homologous gene of the AR15G-90-3 gene (or the AR15G-90B-15 gene) can be obtained by a genetic recombination technique for use in obtaining a homologous gene of a gene whose nucleotide sequence has been already known.

The polynucleotide according to the present invention may have only the region that encodes the endoglucanase catalytic domain, or may also have a region that encodes a cellulose-binding module, a linker sequence, various types of signal peptides, various types of tags, or the like, in addition to the aforementioned region.

[Expression Vector]

The expression vector according to the present invention is incorporated with the aforementioned polynucleotide according to the present invention, and is able to express a polypeptide having hydrolytic activity using CMC as a substrate at least under conditions of a temperature of 110° C. and a pH of 4.0 in a host cell. That is, it is an expression vector which is incorporated with the aforementioned polynucleotide according to the present invention in a state where the aforementioned hyperthermostable endoglucanase according to the present invention can be expressed. More specifically, it is necessary for the expression vector to be incorporated with an expression cassette including, from the upstream, DNA having a promoter sequence, the aforementioned polynucleotide according to the present invention, and DNA having a terminator sequence. It should be noted that the incorporation of the polynucleotide into the expression vector can be performed by using a well-known genetic recombination technique. It is also possible to use a commercially available expression vector preparation kit for the incorporation of the polynucleotide into the expression vector.

In the present invention and the description of this application, an "expression vector" is a vector including, from upstream, DNA having a promoter sequence, DNA having a sequence for incorporating foreign DNA, and DNA having a terminator sequence.

The expression vector may be a vector to be introduced into a prokaryotic cell such as *E. coli*, or to be introduced into a eukaryotic cell such as a yeast, a filamentous fungus, a cultured insect cell, a cultured mammalian cell, or a plant cell. Regarding such an expression vector, an arbitrary expression vector for usual use can be adopted corresponding to the respective host.

It is preferable that the expression vector according to the present invention is an expression vector incorporated with not only the aforementioned polynucleotide according to the present invention but also a drug resistance gene or the like. This is because it makes it easy to screen host cells transformed by the expression vector and untransformed host cells.

The drug resistance gene can be exemplified by a kanamycin resistance gene, a hygromycin resistance gene, a bialaphos resistance gene, or the like.

[Transformant]

The transformant according to the present invention is introduced with the above-mentioned expression vector according to the present invention. In the aforementioned transformant, the hyperthermostable endoglucanase according to the present invention can be expressed. The host to introduce the expression vector may be a prokaryotic cell such as *E. coli* or a eukaryotic cell such as a yeast, a filamentous fungus, a cultured insect cell, a cultured mammalian cell, or a plant cell. That is, the transformant according to the present invention is *E. coli*, a yeast, a filamentous fungus, a cultured insect cell, a cultured mammalian cell, a plant cell, or the like which is introduced with the expression vector according to the present invention.

By culturing a transformant of *E. coli*, the hyperthermostable endoglucanase according to the present invention can be produced more easily and conveniently with high yield. On the other hand, because proteins are hydrolyzed in eukaryotic cells, a hyperthermostable endoglucanase which is more thermostable can be produced by using a transformant of a eukaryotic cell rather than by using a transformant of a prokaryotic cell.

The method to produce the transformant using the expression vector is not particularly limited, and a method for usual use in the production of transformants can be conducted. The concerned method can be exemplified by a heat shock method, an *Agrobacterium*-mediated method, a particle gun method, an electroporation method, a PEG (polyethylene glycol) method, and the like. Of these, if the host is a plant cell, a particle gun method or an *Agrobacterium*-mediated method is preferred.

If a prokaryotic cell, a yeast, a filamentous fungus, a cultured insect cell, a cultured mammalian cell, or the like is used as a host, the obtained transformant is generally able to be cultured by a usual method in the same manner as that of the untransformed host.

[Method for Producing a Hyperthermostable Endoglucanase]

The method for producing a hyperthermostable endoglucanase according to the present invention is a method to produce a hyperthermostable endoglucanase in the aforementioned transformant according to the present invention. When culturing a transformant produced by using the expression vector incorporated with the aforementioned polynucleotide according to the present invention on the downstream of a promoter which has no ability to regulate the timing of the expression or the like, in the transformant, the hyperthermostable endoglucanase according to the present invention is expressed constitutively. On the other hand, for the transformant produced by using a so-called expression inducible promoter to induce the expression by means of a specific compound, temperature condition, or the like, the hyperthermostable endoglucanase is expressed in the concerned transformant by culturing the transformant and conducting an induction treatment suitable for the respective expression-inducing condition.

The hyperthermostable endoglucanase produced by the transformant may be used in a state of being retained in the transformant, or may be extracted/purified from the transformant.

The method to extract or purify the hyperthermostable endoglucanase according to the present invention from the transformant is not particularly limited as long as the method does not deteriorate the glycoside hydrolysis activity of the hyperthermostable endoglucanase, and the extraction can be done by a method for usual use in the extraction of a polypeptide from cells or biological tissues. The method can be exemplified by a method in which the transformant is immersed in an appropriate extraction buffer to extract the hyperthermostable endoglucanase, and thereafter the liquid extract and the solid residue are separated. The extraction buffer preferably contains a solubilizing agent such as a surfactant. If the transformant is a plant, the transformant may be previously shredded or crushed before immersing in an extraction buffer. Moreover, as the method for separating the liquid extract and the solid residue, for example, a publicly known solid-liquid separation treatment such as a filtration method, a compression filtration method, or a centrifugation treatment method may be used, or the transformant immersed in an extraction buffer may be squeezed. The hyperthermostable endoglucanase in the liquid extract can be purified by using a publicly known purification method such as a salting-out method, an ultrafiltration method, or a chromatography method.

If the hyperthermostable endoglucanase according to the present invention is expressed while the secretory signal peptide is held in the transformant, a solution containing the hyperthermostable endoglucanase can be easily and conveniently obtained by culturing the transformant and thereafter recovering a culture liquid supernatant made by removal of the transformant from the obtained culture product. Moreover, if the hyperthermostable endoglucanase according to the present invention has a tag such as a His tag, the hyperthermostable endoglucanase in a liquid extract or in a culture supernatant can be easily and conveniently purified by an affinity chromatography method using the tag.

In other words, the method for producing a hyperthermostable endoglucanase according to the present invention includes the culturing of the transformant according to the present invention to produce a hyperthermostable endoglucanase within the transformant, and, according to need, the extraction and purification of the hyperthermostable endoglucanase from the transformant.

[Glycoside Hydrolase Mixture]

The glycoside hydrolase mixture according to the present invention can also be used as a mixture containing the aforementioned hyperthermostable endoglucanase according to the present invention, or a hyperthermostable endoglucanase produced by the aforementioned method for producing a hyperthermostable endoglucanase according to the present invention, and at least one or more types of other glycoside hydrolases. The hyperthermostable endoglucanase produced by the aforementioned method for producing a hyperthermostable endoglucanase according to the present invention may be in a state of being included in the transformant, or may be extracted or purified from the transformant. By using the hyperthermostable endoglucanase according to the present invention as a mixture with other glycoside hydrolases in the reaction to hydrolyze polysaccharides, persistent lignocelluloses can be more efficiently degraded.

The other glycoside hydrolase than the aforementioned hyperthermostable endoglucanase to be contained in the glycoside hydrolase mixture is not particularly limited as long as it has lignocellulose hydrolysis activity. The other glycoside hydrolase than the aforementioned hyperthermostable endoglucanase to be contained in the glycoside hydrolase mixture can be exemplified by hemicellulases such as xylanase and β-xylosidase, cellobiohydrolase, β-glucosidase, endoglucanase, or the like. In addition to the hyperthermostable endoglucanase, the glycoside hydrolase mixture according to the present invention is preferably a mixture containing at least either one of glycoside hydrolases (i.e., a hemicellulase or an endoglucanase), and is more preferably a mixture containing both glycoside hydrolases (i.e., a hemicellulase and an endoglucanase). Among them, a mixture containing, in addition to the aforementioned hyperthermostable endoglucanase, at least one type of glycoside hydrolases selected from the group consisting of xylanase, β-xylosidase, cellobiohydrolase, and β-glucosidase is preferred; and a mixture containing, in addition to the aforementioned hyperthermostable endoglucanase, all of glycoside hydrolases (i.e., xylanase, β-xylosidase, cellobiohydrolase, and β-glucosidase) is more preferred.

The other glycoside hydrolase to be contained in the glycoside hydrolase mixture is preferably a thermostable glycoside hydrolase having glycoside hydrolase activity at least at a temperature of 85° C., and more preferably a thermostable glycoside hydrolase having glycoside hydrolase activity at a temperature of 70 to 90° C. When all the enzymes contained in the glycoside hydrolase mixture are thermostable (for example, the optimum temperature of the enzyme activity or the thermal denaturation temperature of the enzyme protein is 70° C. or higher), the reaction to degrade lignocelluloses with the glycoside hydrolase mixture can be efficiently conducted under a high temperature condition. That is, if the glycoside hydrolase mixture contains only thermostable glycoside hydrolases, it becomes possible, by using the glycoside hydrolase mixture for a lignocellulose hydrolysis process, to conduct the lignocellulose hydrolysis reaction under a high temperature environment where the hydrolysis temperature is from 70 to 90° C. (high temperature hydrolysis). With this high temperature hydrolysis, the amount of enzymes and the time for hydrolysis can be remarkably reduced, and the cost for hydrolysis can be largely cut out.

[Method for Producing a Lignocellulose Degradation Product]

The method for producing a lignocellulose degradation product according to the present invention is a method to obtain a lignocellulose degradation product by hydrolyzing a material composed of lignocellulose containing cellulose with the hyperthermostable endoglucanase according to the present invention to produce oligosaccharides. More specifically, a material composed of lignocellulose containing hemicellulose or cellulose is brought into contact with the hyperthermostable endoglucanase according to the present invention, the transformant according to the present invention, a hyperthermostable endoglucanase produced by the method for producing a hyperthermostable endoglucanase according to the present invention, or the glycoside hydrolase mixture according to the present invention, thereby producing a lignocellulose degradation product containing the degradation product of the aforementioned hemicellulose or cellulose.

It should be noted that, more specifically, the term "degradation product of hemicellulose or cellulose" used herein refers to the product generated as a result of the cleavage of the glycosidic bond of hemicellulose or cellulose.

Another aspect of the method for producing a lignocellulose degradation product according to the present invention is a method in which a material composed of lignocellulose containing hemicellulose or cellulose is brought into contact with the hyperthermostable endoglucanase according to the present invention, the transformant according to the present invention, or a hyperthermostable endoglucanase produced by the method for producing a hyperthermostable endoglucanase according to the present invention, to thereby produce a product generated mainly as a result of the cleavage of the glycosidic bond sites of cellulose.

Yet another aspect of the method for producing a lignocellulose degradation product according to the present invention is a method in which a material composed of lignocellulose containing hemicellulose or cellulose is brought into contact with the glycoside hydrolase mixture according to the present invention, to thereby produce a product generated as a result of the cleavage of the glycosidic bond of hemicellulose or cellulose.

The material composed of lignocellulose containing hemicellulose or cellulose is not particularly limited as long as it contains hemicellulose or cellulose. Such a material can be exemplified by cellulose-based biomass such as a weed and an agricultural waste, used paper, or the like. The aforementioned material containing hemicellulose or cellulose is preferably subjected to a physical treatment such as crushing or shredding, a chemical treatment with an acid, alkali, or the like, or a treatment such as immersing in an appropriate buffer or a dissolution treatment, or the like, prior to being brought into contact with the hyperthermostable endoglucanase according to the present invention.

The reaction condition of the hydrolysis reaction of material composed of lignocellulose containing hemicellulose or cellulose by means of the hyperthermostable endoglucanase according to the present invention may suffice if the condition allows the hyperthermostable endoglucanase to exhibit endoglucanase activity, and is preferable if the condition allows the hyperthermostable endoglucanase to exhibit endoglucanase activity and xylanase activity. For example, it is preferable to conduct the reaction at a temperature of 60 to 160° C. and a pH of 3 to 8, more preferable to conduct the reaction at a temperature of 80 to 120° C. and a pH of 5.0 to 8.0, and still more preferable to conduct the reaction at a temperature of 90 to 110° C. and a pH of 4.0 to 7.0. The reaction time of the hydrolysis reaction is appropriately adjusted in consideration of the type, the method of pretreatment, the amount, or the like, of the material composed of lignocellulose containing hemicellulose or cellulose, to be supplied to the hydrolysis. For example, the hydrolysis reaction can be carried out in a reaction time of 10 minutes to 100 hours, and 1 to 100 hours when degrading the cellulose-based biomass.

For the hydrolysis reaction of the material composed of lignocellulose containing hemicellulose or cellulose, it is also preferable to use at least one or more types of other glycoside hydrolases, in addition to the hyperthermostable endoglucanase according to the present invention. The other glycoside hydrolase may be the same as the glycoside hydrolase that can be contained in the aforementioned glycoside hydrolase mixture, and it is preferable to be a thermostable glycoside hydrolase having glycoside hydrolase activity at least at a temperature of 85° C., and preferably at least at a temperature of 70 to 90° C. In addition, one aspect of the method for producing a lignocellulose degradation product is the use of the hyperthermostable endoglucanase according to the present invention, the transformant according to the present invention, or a hyperthermostable endoglucanase produced by the method for producing a hyperthermostable endoglucanase according to the present invention, and another aspect is the use of the aforementioned glycoside hydrolase mixture.

EXAMPLES

Next is a more detailed description of the present invention with reference to Examples. However, the present invention is not to be limited to the following Examples.

Example 1

Cloning of Novel Hyperthermostable Endoglucanase from Hot Spring Soil

<1> DNA Extraction from Hot Spring Soil and Whole Genome Sequencing (WGS)

With the purpose of searching for genes of hyperthermostable endoglucanase, soil DNA was collected from neutral to weakly alkaline hot springs and subjected to nucleotide sequencing of the metagenomic DNA of the microbiota constituting the soil.

As the soil sample from neutral to weakly alkaline hot springs, hot spring water containing soil, clay, and biomat was collected from five sampling points having gushing high temperature outdoor hot springs in three areas in Japan (metagenomic DNA samples N2, AR19, AR15, OJ1, and H1). These hot spring soil samples were within a range of temperature from 58 to 78° C. and a pH of 7.2 to 8 at the time of the collection.

DNA was extracted from 10 g of each of the collected hot spring soil samples by using the DNA extraction kit (ISOIL Large for Beads ver. 2, manufactured by NIPPON GENE Co., Ltd.). 5 μg of the extracted DNA was subjected to shotgun sequencing of the metagenomic DNA by using the sequencer GS FLX Titanium 454 manufactured by Roche Diagnostics K.K. The remaining DNA was used for PCR cloning of the endoglucanase gene.

The metagenomic DNA sequencing was carried out using the hot spring soil sample AR15. By so doing, a data set of the whole genome sequence (WGS) with an average read length of 370 bp, a total read number of 5,419,406, and a total quantity of sequenced genomes of 2,007,725,040 bp, was obtained.

<2> Assembling and Statistics of Hot Spring Metagenomic Data

Regarding the nucleotide sequence that had been read by the 454 sequencer, the output from the Roche 454 (sff file) was rebasecalled with the PyroBayes (Quinlan et al., Nature Methods, 2008, vol. 5, p. 179-81.), by which sequence files and quality files in FASTA format were obtained. After clipping their ends to improve the quality, the obtained sequence reads were assembled with use of the assembly software, Newbler version 2.3 of 454 Life Sciences. The assembling was performed by setting "minimum acceptable overlap match (mi)=0.9", and "option:-large (for large or complex genomes, speeds up assembly, but reduces accuracy.)".

The total length of the contigs that had been assembled into 100 bp or longer was 118,600,846 bp in total. This data set was used for the cellulase enzyme gene analysis. Out of the total read number of 5,419,406 reads, 4,805,640 reads were assembled into 1,146 bp or longer contigs in average (103.508 contigs in total). Of these, the longest contig length was 151,585 bp.

<3> Prediction of Open Reading Frames (ORFs) of Endoglucanase

The sequences of EC numbers of 3.2.1.4 (cellulase), 3.2.1.21 (β-glucosidase), 3.2.1.37 (β-xylosidase), 3.2.1.91 (cellulose 1,4-β-cellobiosidase), and 3.2.1.8 (endo 1,4-β-xylanase) were downloaded from the UniProt database (http://www.uniprot.org/) (the date of access: 2011 Dec. 9), and the proteome local database of these glycoside hydrolase genes was constructed. Using the annotation software Orphelia (Hoff et al., Nucleic Acids Research, 2009, 37 (Web Server issue: W101-W105), gene regions (=open reading frames) were predicted from the contig sequences obtained from the above-mentioned process <2> (Orphelia option: default (model=Net700, maxoverlap=60). In order to extract the glycoside hydrolase gene from the predicted ORF, the aforementioned local database using BLASTP (blastall ver. 2.2.18) was referred to. Optional conditions of BLASTP were set such that: "Filter query sequence=false", "Expectation value (E)<1e$^{-20}$" [hereunder, the default values: Cost to open a gap=-1, Cost to extended gap=-1, X dropoff value for gapped alignment=0, Threshold for extending hits=0, and Word size=default], and the hit ORF sequences were collected as glycoside hydrolase genes. The collected nucleotide sequences included the genes of glycoside hydrolases such as cellulases, endohemicellulases, and debranching enzymes.

<4> Classification of Genes into Glycoside Hydrolase (GH) Families

The nucleotide sequences that had been collected in the above-mentioned process <3> were subjected to functional classification, with reference to the protein functional region sequence database of pfam HMMs (Ptam version 23.0 and HMMER v2.3; Finn et al., Nucleic Acids Research Database, 2010, Issue 38, p. D211-222). More specifically, the glycoside hydrolase (GH) families were determined for each of the nucleotide sequences that had been collected in the above-mentioned process <3> by the homology with the Pfhm domain database by using the protein motif search program HMMER (Durbin et al., "The theory behind profile HMMs. Biological sequence analysis: probabilistic models of proteins and nucleic acids", 1998, Cambridge University Press; hmmpfam (Ver. 2.3.2), E-value cutoff <1e$^{-5}$; Database=Pfam_fs (models that can be used to find fragments of the represented domains in a sequence.)). It should be noted that those that covered 70% or more of the sequence of GH catalytic domain were counted as enzyme genes belonging to the respective families.

Through the homology search by BLASTP by using the sequence data of metagenome AR15, 106 ORFs hit as the endoglucanase sequence were predicted as endoglucanase genes. The GH family classification of these 106 ORFs is shown in Table 1. As shown in Table 1, 13 full-length ORFs of endoglucanase genes belonging to the GH5 family, 4 full-length ORB of endoglucanase genes belonging, to the GH9 family, and 4 full-length ORFs of endoglucanase genes belonging to the GH12 family were obtained from the metagenome AR15. Primers were designed for all of these full-length ORFs having been predicted as endoglucanase genes, and these genes were cloned from the hot spring soil metagenomic DNA by PCR. As a result, an endoglucanase gene was isolated from AR15G-90 which was an ORF belonging to the GH12 family and having an endoglucanase gene sequence.

TABLE 1

| | GH family classification of endoglucanase genes | | | | | |
|---|---|---|---|---|---|---|
| AR19 metagenome | GH5 | GH9 | GH12 | GH48 | Other GH families | Total |
| Full-length ORFs | 13 | 4 | 4 | 0 | 40 | 61 |
| Incomplete ORFs | 3 | 3 | 1 | 1 | 37 | 45 |
| Total number of ORFs | 16 | 7 | 5 | 1 | 77 | 106 |

<5> Open Reading Frame AR15G-90

The open reading frame AR15G-90 encoded a polypeptide including 283 amino acid residues and was an incomplete sequence (SEQ ID NO: 1), such that the polypeptide started from valine (V) which was an amino acid residue at position 1, and the 3' end of the nucleotide sequence encoding the polypeptide ended with a termination codon. From the sequence homology of motifs, in the polypeptide encoded by the open reading frame AR15G-90, it was predicted that 171 amino acid residues from glycine (G) at position 101 to leucine (L) at position 271 were the catalytic domain of the glycoside hydrolase family 12. The already known amino acid sequence which showed the highest sequence identity with the amino acid sequence encoded by the above ORF was that of a glycoside hydrolase family 12 (Genbank: ADM27292.1) of *Ignisphaera aggregans* DSM17230 in the phylum Crenarchaeota. Since the homology between the two amino acid sequences that was calculated by the ClustalW algorithm was 56% for the total length and 64% for the GH12 catalytic domain, the aforementioned ORF was verified as a novel sequence.

FIG. 1 shows an alignment of the amino acid sequence of the polypeptide encoded by the open reading frame AR15G-

90 and the amino acid sequence (SEQ ID NO: 8) of a glycoside hydrolase family 12 of *Ignisphaera aggregans* DSM17230. In FIG. 1, the black/white inverted amino acids denote the same amino acid residues (identical) throughout all of these amino acid sequences, and the symbols "-" denote deletions (gaps).

<6> Gene Cloning from Open Reading Frame AR15G-90

PCR was conducted using a hot spring soil DNA that had been amplified by the genomic DNA amplification kit (GenomiPhi V2 DNA Amplification Kit, manufactured by GE Healthcare) as a template, and by using a forward primer composed of the nucleotide sequence represented by SEQ ID NO: 7 (5'-CACCATGGTGACCATCACGCCGAGTACA-3': obtained by adding 4 nucleotides (CACC) and the initiation codon (ATG) to the 5'-end side of the nucleotide sequence represented by SEQ ID NO: 5. The nucleotides CACC added on the 5' side is a sequence for insertion into a vector) and a reverse primer composed of the nucleotide sequence represented by SEQ ID NO: 6 (5'-CTACCTCAGTGTTTTACCTGGC-3'). The nucleotide sequence represented by SEQ ID NO: 5 is a nucleotide sequence which is homologous (identical) with a partial sequence including the nucleotides at position 1 to 21 of the nucleotide sequence represented by SEQ ID NO: 2. Moreover, the nucleotide sequence represented by SEQ ID NO: 6 is a nucleotide sequence which is complementary with a partial sequence including the nucleotides at position 831 to 852 of the nucleotide sequence represented by SEQ ID NO: 2. The amplified PCR products were inserted in the pET101/D-TOPO vector of Champion pET Directional TOPO Expression Kits (manufactured by Life Technologies), and transformed into the One Shot TOP10 strain. Positive clones were selected by colony PCR, and then cultured in a LB liquid medium containing 100 mg/L ampicillin at a temperature of 37° C. and 200 rpm for 17 to 20 hours, followed by the preparation of plasmids using the miniprep kit (Wizard plus SV Minipreps DNA Purification System, manufactured by Promega). The prepared plasmids were sequenced by using the 3730 DNA Analyzer sequencer of Life Technologies.

Five gene clones AR15G-90-2, AR15G-90-3, AR15G-90-9, AR15G-90-12, and AR15G-90-13 were obtained from the open reading frame AR15G-90 by PCR cloning. The nucleotide sequence of the endoglucanase candidate gene AR15G-90-3 (SEQ ID NO: 4) contained 852 bp like that of the open reading frame AR15G-90 (SEQ ID NO: 2), and was different from that of the ORF by 4 nucleotides. That is, the 93th nucleotide was T (thymine) in the open reading frame AR15G-90, whereas it was C (cytosine) in the cloned AR15G-90-3 gene; the 335th nucleotide was G (guanine) in the open reading frame AR15G-90, whereas it was A (adenine) in the cloned AR15G-90-3 gene; the 652th nucleotide was G in the open reading frame AR15G-90, whereas it was A in the cloned AR15G-90-3 gene; and the 699th nucleotide was G in the open reading frame AR15G-90, whereas it was A in the cloned AR15G-90-3 gene. Of these, differences in nucleotides at two locations also resulted in different amino acids, and the amino acid sequence of the open reading frame AR15G-90 (SEQ ID NO: 1) and the amino acid sequence of the endoglucanase candidate gene AR15G-90-3 (SEQ ID NO: 3) were different by 2 amino acid residues. That is, the amino acid residue at position 112 was arginine (R) in the open reading frame AR15G-90, whereas it was lysine (K) in the cloned AR15G-90-3 gene; and the amino acid residue at position 218 was valine (V) in the open reading frame AR15G-90, whereas it was isoleucine (I) in the cloned AR15G-90-3 gene.

<7> Gene Expression of AR15G-90-3 Gene and Purification of Enzymatic Protein

A protein obtained by adding a histidine tag on the C-end side was used for the purification of the enzymatic protein. A sequence added with a histidine tag was prepared by inserting the endoglucanase candidate gene AR15-90-3 from which the stop codon was removed into the pET101/D-TOPO vector. The plasmids having the target gene added with the tag sequence were introduced in *E. coli* for protein expression by a heat shock method. The Rosetta-gamiB (DE3) pLysS strain (manufactured by Merck) was used as the competent cell for the transformation. *E. coli* having the target gene was inoculated in a LB medium containing 100 mg/L ampicillin and cultured to about $OD_{600}=0.2$ to 0.8, which was then added with IPTG (isopropyl-β-D(-)-thiogalactopyranoside), and additionally cultured for 5 to 20 hours. By so doing, the expression induction of the target protein was carried out. After the culture, *E. coli* was collected by centrifugation, to which 50 mM Tris-HCl buffer (pH8.0) of ⅒-fold volume of the culture liquid was added and suspended. Thereafter, 5 minutes disrupting and 5 minutes halting processes were repeated 7 to 8 times by using an ultrasonic disruption apparatus, Astrason 3000 (manufactured by Misonix, Inc.). By so doing, the crude extract of the gene recombinant *E. coli* containing the target protein was obtained. The crude extract of the gene recombinant *E. coli* was filtrated through a filter (pore diameter ϕ=0.45 μm, manufactured by Millipore), and the yielded filtrate was used as a gene recombinant *E. coli* homogenate supernatant.

NaCl was added to the gene recombinant *E. coli* homogenate supernatant to a final concentration of 500 mM, and the resulting mixture was loaded onto an ion-exchange column HisTrap FF (manufactured by GE Healthcare) equilibrated with 50 mM Tris-HCl buffer (pH8.0) containing 500 mM of NaCl, by which proteins were fractionated with 0 to 100% concentration gradient with 50 mM Tris-HCl buffer (pH8.0) containing 500 mM of NaCl and 500 mM of imidazole using a middle-to-high pressure liquid chromatography system AKTA design (manufactured by GE Healthcare).

The fractions exhibiting CMC hydrolysis activity were all mixed and then subjected to solution exchange into 50 mM Tris-HCl buffer (pH8.0) containing 750 mM ammonium sulfate using a centrifugal ultrafiltration membrane VIVASPIN 20 (manufactured by Sartorius stedim). The fractions with CMC hydrolysis activity after the solution exchange were loaded onto a hydrophobic interaction separation column HiTrap Phenyl HP (manufactured by GE Healthcare) equilibrated with the same solution, by which proteins were fractionated with 0 to 100% concentration gradient with 50 mM Tris-HCl buffer (pH18.0). The fractions exhibiting CMC hydrolysis activity were all mixed and then concentrated by using the VIVASPIN 20 until the liquid volume reached to about 8 mL. The concentrated sample was loaded onto a gel filtration column Hiload 26/60 superdex 200 pg (manufactured by GE Healthcare) equilibrated with 50 mM Tris-HCl buffer (pH8.0) containing 150 mM NaCl, and fractionated by flowing the same buffer of 1 to 1.5 fold volume of the column volume at a flow rate of 2 to 3 mL/min. The fractions exhibiting CMC hydrolysis activity were all mixed and then subjected to solution exchange into 50 mM Tris-HCl buffer (pH8.0) and concentrated. By so doing, a purified enzyme having the final concentration of about 1 mg/mL was obtained.

The gene recombinant *E. coli* homogenate supernatant and the purified enzyme were checked by SDS-PAGE (SDSpolyacrylamide gel electrophoresis) analysis. 5 μg of the aforementioned homogenate supernatant and 0.5 μg of the purified enzyme were mixed with a four times concentrated solution of 2-mercaptoethanol containing sample buffer (manufactured by Wako Pure Chemical industries, Ltd.) such that the buffer concentration was one times, and then treated at a temperature of 95° C. for 4 minutes, followed by electrophoresis by using a 10% Criterion TGX Stain-free Gel (manufactured by Bio-Rad Laboratories, Inc.). After the completion of the electrophoresis, the protein bands were visualized by the imaging system ChemiDoc (manufactured by Bio-Rad Laboratories, Inc.).

FIG. 2 shows the SDS-PAGE analysis result of the gene recombinant E. coli homogenate supernatant prepared from the transformed E. coli introduced with the AR15G-90-3 gene and the purified enzyme which was purified from the gene recombinant E. coli homogenate supernatant. The lane 1 is a molecular weight marker for proteins, and the lanes 2 and 3 show the electrophoresis patterns of the gene recombinant E. coli homogenate supernatant and the purified enzyme, respectively. As a result, in the gene recombinant E. coli homogenate supernatant (lane 2), a band was observed near the molecular weight of 35.6 kDa predicted from the amino acid sequence (SEQ ID NO: 3) and the histidine tag of the pET101/D-TOPO vector. In the purified enzyme (lane 3), although two weak bands were detected along with a strong band corresponding with the above band, it was confirmed that the major protein contained was the aforementioned enzymatic protein (indicated by an arrow in the figure).

<8> Measurement of CMC Hydrolysis Activity of AR15G-90-3

First, the CMC hydrolysis activity of the enzymatic protein (AR15G-90-3) encoded by the AR15G-90-3 gene was investigated using CMC (carboxymethyl cellulose, manufactured by Sigma-Aldrich Co. LLC.) as a substrate.

The measurement of the CMC hydrolysis activity of the gene recombinant E. coli homogenate supernatant obtained from the above-mentioned process <7> or the enzyme sample in the middle of purification was carried out by allowing a mixture solution composed of 100 μL of a 1 mass % CMC aqueous solution, 50 μL of 200 mM acetic acid buffer (pH4.0), and 50 μL of either the gene recombinant E. coli homogenate supernatant or the enzyme sample in the middle of purification, to react at a temperature of 40 to 99° C. for 10 to 15 minutes.

In all the measurements, a mixture solution prepared by adding 50 mM Tris-HCl buffer (pH8.0) instead of the gene recombinant E. coli homogenate supernatant or the purified enzyme sample and reacting under the same conditions was used as the control lot. Moreover, the substrate solution and the enzyme were respectively and separately kept at retained reaction temperatures for 5 minutes, and then mixed. This timing was set to the initiation of the reaction. After the completion of the reaction, the same volume of a 3,5-dinitrosalicylic acid reagent (DNS solution) was added. The mixture was treated by heating at a temperature of 100° C. for 5 minutes, cooled down on ice for 5 minutes, and then centrifuged at 17,400 g for 5 minutes. By so doing, the supernatant was obtained. The absorbance at 540 nm was measured by using a spectrophotometer, and the amount of reduced sugar in the supernatant was calculated by using a calibration curve prepared with glucose. The amount of reduced sugar produced by the enzymatic hydrolysis was obtained by the difference from the control lot. The enzymatic activity for producing 1 μmol of reduced sugar per minute was defined as 1 U, and the value obtained by dividing it by the amount of protein was defined as the specific activity (U/mg).

<9> Substrate Specificity of AR15G-90-3

The hydrolysis activities for various cellulose substrates and hemicellulose substrates were investigated with the enzymatic protein (AR15G-90-3) encoded by the AR15G-90-3 gene. In the measurement, the purified enzyme solution (0.2 mg/mL) obtained from the above-mentioned process <7> was used. In addition, as substrates, PSA, an Avicel powder (fine crystalline cellulose powder, manufactured by Merck), CMC (manufactured by Sigma-Aldrich Co. LLC.), xylan (derived from beechwood, manufactured by Sigma-Aldrich Co. LLC.), lichenan (manufactured by MP Biomedicals, LLC.), laminarin (derived from *Laminaria digitata*, manufactured by Sigma-Aldrich Co. LLC.), PNPC (manufactured by Sigma-Aldrich Co. LLC.), PNPX (manufactured by Sigma-Aldrich Co. LLC.), and PNPG (manufactured by Sigma-Aldrich Co. LLC.) were used.

PSA was prepared by once dissolving an Avicel powder (fine crystalline cellulose powder, manufactured by Merck) with a phosphoric acid solution, then precipitating it by adding sterile purified water, and thereafter washing the same until the pH reached 5 or higher. It should be noted that PSA used for all the following experiments was prepared by the above method.

More specifically, the enzymatic reaction was carried out by first preincubating a mixture solution composed of 50 μL of 200 mM acetic acid buffer (pH4.0) (McIlvaine buffer (pH7.0) in the case of xylan), 5 μL of the purified enzyme solution (0.2 mg/mL) and 45 μL of purified water as a reaction solution at a temperature of 70° C. for 5 minutes, then additionally adding 100 μL of each substrate solution (1% by mass aqueous solutions of PSA, Avicel powder, CMC, xylan, lichenan and laminarin, and 3.4 mM aqueous solutions of PNPG, PNPX, and PNPC) whose temperature was kept in the same manner thereto, and incubating the resulting mixture solution at a temperature of 70° C. for 20 minutes. In the reaction, the mixture solution was stirred by applying vibration of 1,400 rpm using the Thermomixer (manufactured by Eppendorf) so as to avoid the precipitation of insoluble substrates. In all the measurements, a mixture solution prepared by adding 50 mM Tris-HCl buffer (pH8.0) in place of the purified enzyme solution and reacting under the same conditions was used as the control lot.

After the completion of the reaction, in the reaction where PSA, Avicel powder, CMC, xylan, lichenan or laminarin was used as the substrate, the amount of reduced sugar produced by the hydrolysis was obtained, and the specific activity (U/mg) was calculated in the same manner as that of the above-mentioned process <8> where the CMC hydrolysis activity of AR15G-90-3 was investigated. However, in the case of xylan, a calibration curve prepared with xylose was used.

In a reaction where PNPG, PNPX, or PNPC was used as a substrate, after the completion of the reaction, the same volume of 200 mM aqueous solution of sodium carbonate was added, and the resulting mixture was centrifuged for 5 minutes. By so doing, the supernatant was obtained. The absorbance at 420 nm was measured by using a spectrophotometer, and the amount of p-nitrophenol in the supernatant was calculated by using a calibration curve prepared using p-nitrophenol. The amount of p-nitrophenol produced by the enzymatic hydrolysis was obtained by the difference from the control lot. The enzymatic activity for producing 1 μmol of p-nitrophenol per minute was defined as 1 U, and the value obtained by dividing it by the amount of protein was defined as the specific activity (U/mg).

Figure 3:
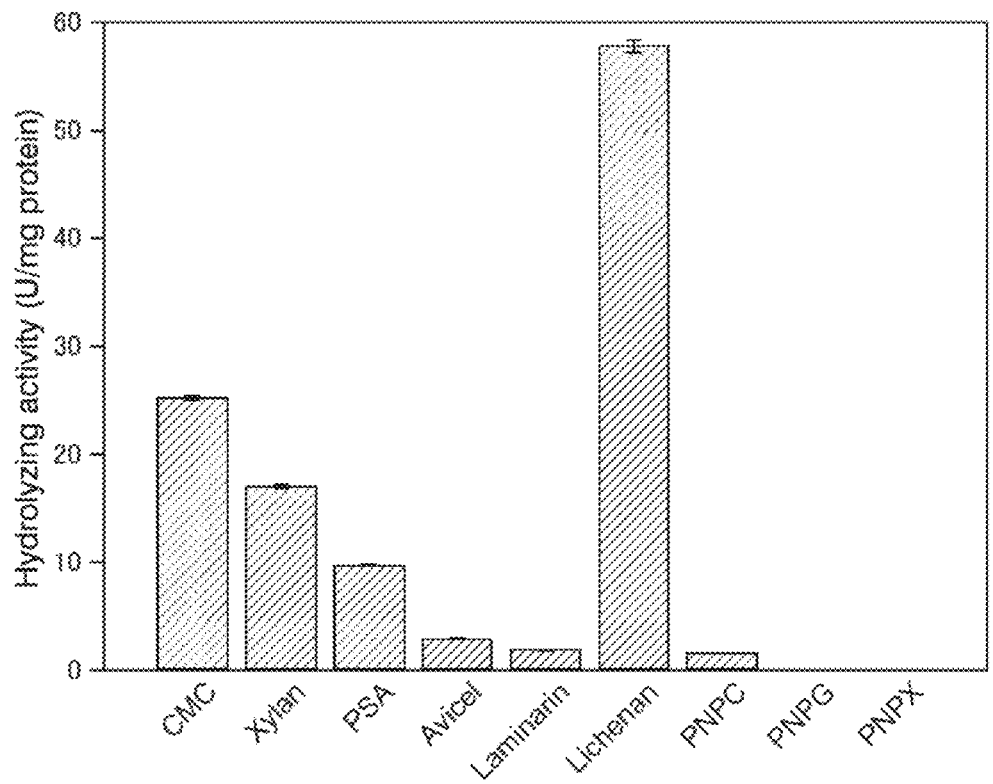
FIG. 3 is a diagram showing the measurement results of the hydrolytic activity of the AR15G-90-3 protein expressed in *E. coli* in Example 1 for each substrate.

Each measurement was performed by three independent experiments, from which the mean value and the standard errors were obtained. The measurement results are shown in FIG. 3. As a result, AR15G-90-3 exhibited hydrolysis activity for CMC, xylan, PSA, and lichenan, although it exhibited a very low level of hydrolysis activity for Avicel, laminarin and PNPC, and exhibited almost no hydrolysis activity for PNPG and PNPX.

<10> Temperature Dependency of CMC Hydrolysis Activity

The temperature dependency of the CMC hydrolysis activity of the enzymatic protein (AR15G-90-3) was investigated. In the measurement, a purified enzyme solution prepared by diluting the purified enzyme obtained from the above-mentioned process <7> to 0.13 mg/mL with 50 mM Tris-HCl buffer (pH8.0) was used. In addition, CMC (carboxymethyl cellulose, manufactured by Sigma-Aldrich Co. LLC.) was used as the substrate.

More specifically, the measurement was conducted by allowing a mixture solution composed of 50 µL of 200 mM acetic acid buffer (pH4.0), 40 µL of 50 mM Tris-HCl buffer (pH18.0), 10 µL of the purified enzyme solution (0.13 mg/mL), and 100 µL of a 1 mass % CMC aqueous solution, to react at a temperature of 60, 70, 80, 90, 100, 110, 120, 130, 140, 150 or 160° C. for 15 minutes. When performing the activity measurement at a temperature of 100° C. or higher, a glass vial, a rubber stopper, and an aluminum seal (manufactured by Nichiden-Rika Glass Co., Ltd.) were used. After the completion of the reaction, the amount of reduced sugar produced by the enzymatic hydrolysis was obtained in the sane manner as in the above-mentioned process <8> to calculate the CMC degradation activity (specific activity) (U/mg). In addition, the CMC degradation activity was measured in a similar manner by adding 0.5 mM of calcium ions to the reaction solution.

Further, the CMC degradation activity was measured in a similar manner by using TrEG (*Trichoderma reesei* EG2; manufactured by Megazyme) and TmEG (*Thermotoga maritima* EG; manufactured by Megazyme) as the known endoglucanases. Regarding the buffer, a 200 mM McIlvaine buffer (pH4.0) and a 200 mM McIlvaine buffer (pH5.0) were used for TrEG and TmEG, respectively, instead of the 200 mM acetic acid buffer, to allow the reaction to proceed at a temperature of 30, 40, 50, 60, 70, 80, 90, or 100° C.

Figure 4:
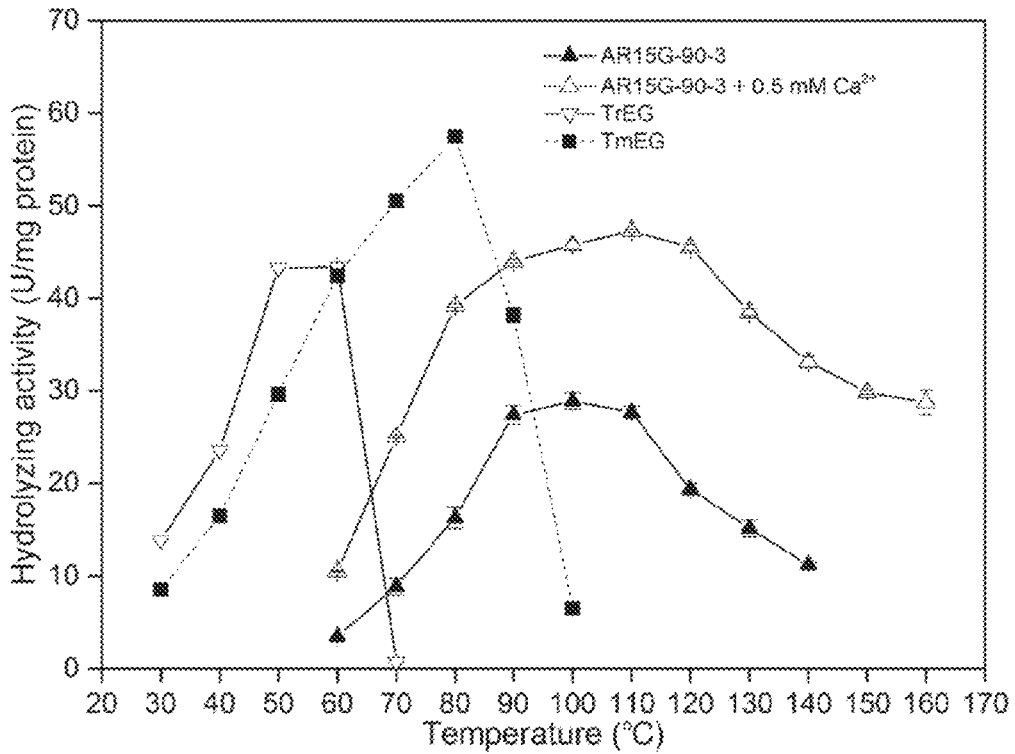
FIG. 4 is a diagram showing the results of the CMC hydrolysis activity (pH4.0) of the AR15G-90-3 protein expressed in *E. coli* in the absence of calcium ions ("AR15G-90-3" in the drawing) and in the presence of calcium ions ("AR15G-90-3+0.5 mM $Ca^{2+}$" in the drawing) and the CMC hydrolysis activity (pH4.0) of TrEG (*Trichoderma reesei* EG2) and of TmEG (*Thermotoga maritima* EG) that were measured at respective temperatures in Example 1.

Each measurement was performed by three independent experiments, from which the mean value and the standard errors were obtained. The measurement results are shown in FIG. 4. AR15G-90-3 exhibited CMC degradation activity in a temperature range of 60 to 160° C. The optimum temperature ($T_{opt}$) showing the highest activity was 100° C. at a pH of 4.0. In addition, when 0.5 mM of calcium ions was added into the enzyme-substrate reaction solution, the $T_{opt}$ was increased to 110° C., and the specific activity at respective temperatures was also increased. On the other hand, the $T_{opt}$ of known endoglucanases was 60° C. for TrEG and 80° C. for TmEG. In other words, AR15G-90-3 had an optimum temperature which was higher than that of the endoglucanase (EG) of a hyperthermophile *T. maritima* by 20° C. or more.

In addition, an improvement in the CMC degradation activity of AR15G-90-3 was observed by the addition of calcium ions in all temperature ranges. In particular, the CMC degradation activity at a temperature of 120° C. or higher showed a gradual downward trend in the presence of calcium ions, and the activity at 140° C. was about 40% of the activity at the optimum temperature in the absence of calcium ions, whereas the activity at 160° C. retained 60% of the activity at the optimum temperature in the presence of calcium ions. This was considered to be the effect brought about by the stabilization of the enzymatic protein by the presence of calcium ions.

<11> pH Dependency of CMC Hydrolysis Activity

The pH dependency of the CMC hydrolysis activity of the enzymatic protein (AR15G-90-3) was investigated. In the measurement, a purified enzyme solution prepared by diluting the purified enzyme obtained from the above-mentioned process <7> to 0.13 mg/mL with 50 mM Tris-HCl buffer (pH8.0) was used. In addition, CMC (carboxymethyl cellulose, manufactured by Sigma-Aldrich Co. LLC.) was used as the substrate.

More specifically, the measurement was conducted by allowing a mixture solution composed of 50 µL of McIlvaine buffer (pH3 to 8), 30 µL of purified water, 20 µL of the purified enzyme solution (0.13 mg/mL), and 100 µL of a 1 mass % CMC aqueous solution, to react at a temperature of 70° C. for 15 minutes. After the completion of the reaction, the amount of reduced sugar produced by the enzymatic hydrolysis was obtained in the same manner as in the above-mentioned process <8> to calculate the CMC hydrolysis activity (specific activity) (U/mg).

Figure 5:
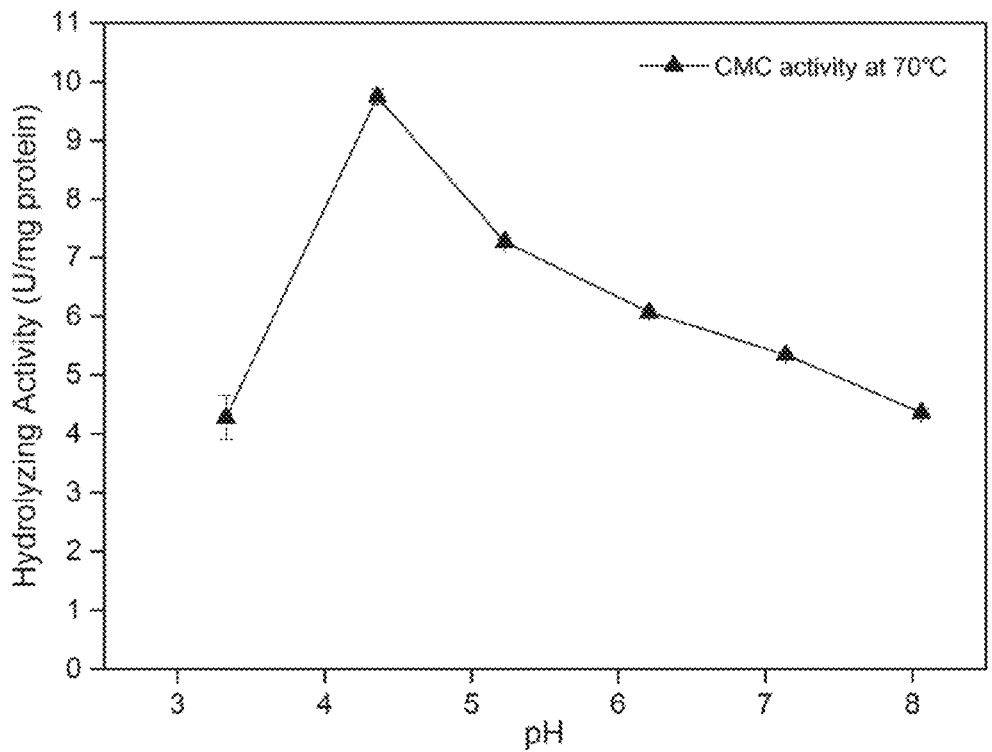
FIG. 5 is a diagram showing the results of the CMC hydrolysis activity (70° C.) of the AR15G-90-3 protein expressed in *E. coli* measured at respective pH values in Example 1.

Each measurement was performed by three independent experiments, from which the mean value and the standard errors were obtained. The measurement results are shown in FIG. 5. The pH was plotted by the actual measurement values of the mixture solution containing the substrate, the buffer, and the enzyme.

AR15G-90-3 exhibited CMC hydrolysis activity in a pH range of 3 to 8.

The optimum pH was a pH of 4.4 (actual measurement value of the mixture solution containing the substrate, the buffer, and the enzyme) at 70° C.

<12> Temperature Dependency of Xylanase Activity

Since AR15G-90-3 also exhibited xylan degradation activity (xylanase activity), the temperature dependency of the xylanase activity was investigated. In the measurement, a purified enzyme solution prepared by diluting the purified enzyme obtained from the above-mentioned process <7> to 0.13 mg/mL with 50 mM Tris-HCl buffer (pH8.0) was used. In addition, xylan (derived from beechwood, manufactured by Sigma-Aldrich Co. LLC.) was used as the substrate.

More specifically, the measurement was conducted by allowing a mixture solution composed of 50 µL of McIlvaine buffer (pH7.0), 20 µL of 50 mM Tris-HCl buffer (pH8.0), 30 µL of the purified enzyme solution (0.13 mg/mL), and 100 µL of a 1 mass % xylan aqueous solution, to react at a temperature of 40, 50, 60, 70, 80, 90, 100, 110, 120, 130 or 140° C. for 15 minutes. When performing the activity measurement at a temperature of 100° C. or higher, a glass vial, a rubber stopper, and an aluminum seal (manufactured by Nichiden-Rika Glass Co., Ltd.) were used. After the completion of the reaction, the amount of reduced sugar by the enzymatic hydrolysis was obtained in the same manner as in the above-mentioned process <8> to calculate the xylanase activity (specific activity) (U/mg), with the exception that a calibration curve prepared with xylose was used for the calculation.

Figure 6:
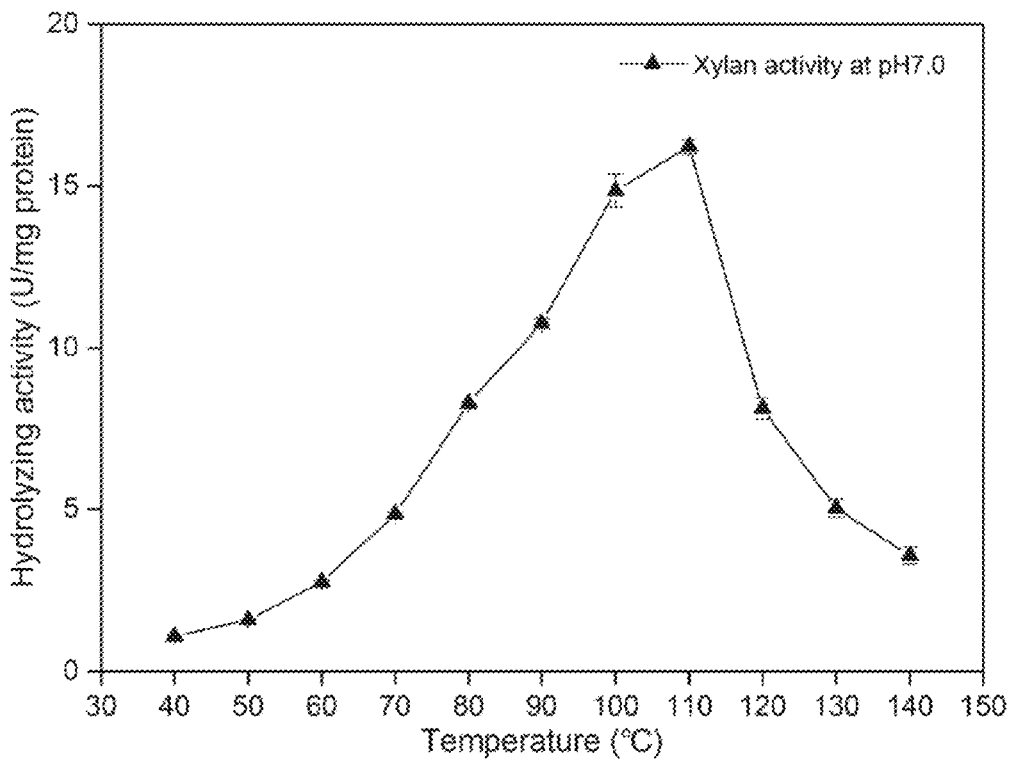
FIG. 6 is a diagram showing the results of the xylanase activity (pH7.0) of the AR15G-90-3 protein expressed in *E. coli* measured at respective temperatures in Example 1.

Each measurement was performed by three independent experiments, from which the mean value and the standard errors were obtained. The measurement results are shown in FIG. 6. AR15G-90-3 exhibited xylanase activity in a temperature range of 40 to 140° C. The optimum temperature ($T_{opt}$) showing the highest activity was 110° C. at a pH of 7.0.

<13> pH Dependency of Xylanase Activity

The pH dependency of the xylanase activity of AR15G-90-3 was investigated. In the measurement, a purified enzyme solution prepared by diluting the purified enzyme obtained from the above-mentioned process <7> to 0.1 mg/mL with 50 mM Tris-HCl buffer (pH8.0) was used. In addition, xylan (derived from beechwood, manufactured by Sigma-Aldrich Co. LLC.) was used as the substrate.

More specifically, the measurement was conducted by allowing a mixture solution composed of 25 μL of Britton-Robinson buffer (pH5 to 10), 15 μL of purified water, 10 μL of the purified enzyme solution (0.1 mg/mL), and 50 μL of a 1 mass % xylan aqueous solution, to react at a temperature of 70° C. for 15 minutes. After the completion of the reaction, the amount of reduced sugar produced by the enzymatic hydrolysis was obtained in the same manner as in the above-mentioned process <12> to calculate the xylanase activity (specific activity) (U/mg).

Figure 7:
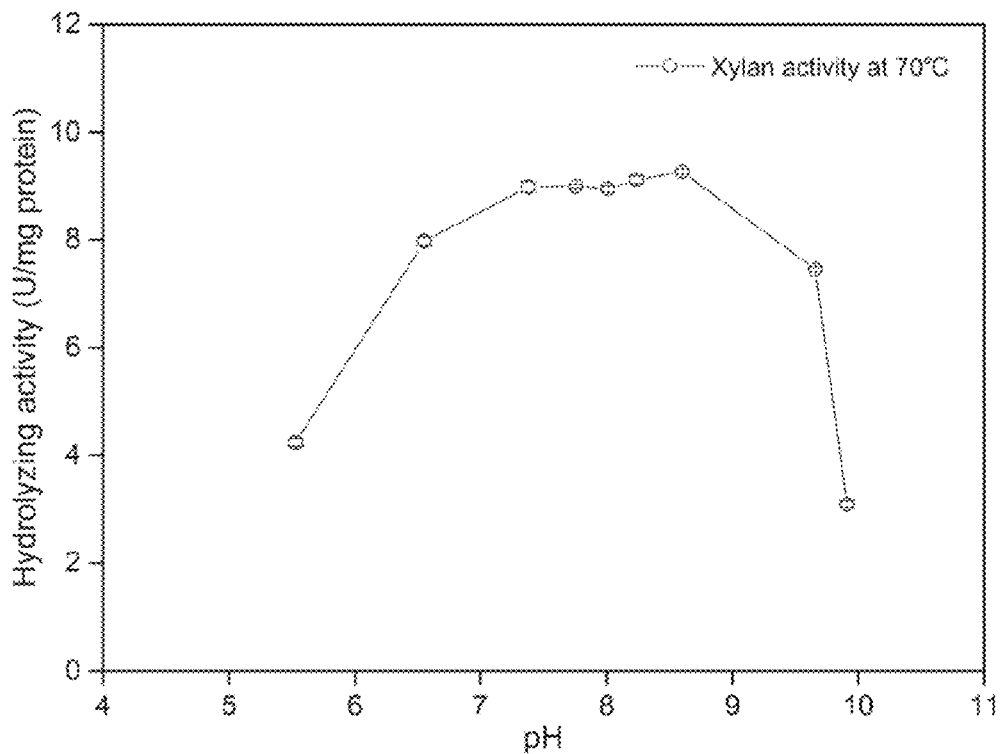
FIG. 7 is a diagram showing the results of the xylanase activity (70° C.) of the AR15G-90-3 protein expressed in *E. coli* measured at respective pH values in Example 1.

Each measurement was performed by three independent experiments, from which the mean value and the standard errors were obtained. The measurement results are shown in FIG. 7. The pH was plotted by the actual measurement values of the mixture solution containing the substrate, the buffer, and the enzyme. AR15G-90-3 exhibited xylanase activity in a pH range of 5 to 10. The optimum pH was a pH of 8.6 (actual measurement value of the mixture solution containing the substrate, the buffer, and the enzyme) at 70° C.

<14> Thermal Stability of AR15G-90-3 Using CMC and Xylan as Substrates

As an indicator associated with the thermal stability of a protein, thermal denaturation temperature or thermal degradation temperature, $T_m$ (melting temperature) is often used. The preincubation temperature $T_{50}$ at which the enzymatic activity is reduced to 50% of that of the nontreated lot by preliminary heating (preincubation) for a certain time is substantially equal to the thermal degradation temperature $T_m$ of the protein, and can be obtained by measuring the enzymatic activity. The thermal degradation temperature $T_m$ of AR15G-90-3 was obtained by this method.

More specifically, the enzymatic reaction was performed after conducting preliminary heating (preincubation) at a temperature of 50 to 130° C. for 30 minutes under a substrate-free condition. The composition of the reaction solution of the enzymatic reaction was the same as that of the above-mentioned process <10> in the case of the CMC substrate, and was the same as that of the above-mentioned process <12> in the case of the xylan substrate, to allow the reaction to proceed for 15 minutes at a temperature of 70° C. The thermal stability of AR15G-90-3 was investigated by using the temperature $T_{50}$ at which the CMC hydrolysis activity or the xylan hydrolysis activity is reduced to 50% as an indicator. Each data was subjected to an approximation using a logistic function, and the temperature at which the approximation curve reached the relative activity value of 50% was defined as $T_{50}$ (that is, $T_m$).

Figure 8:
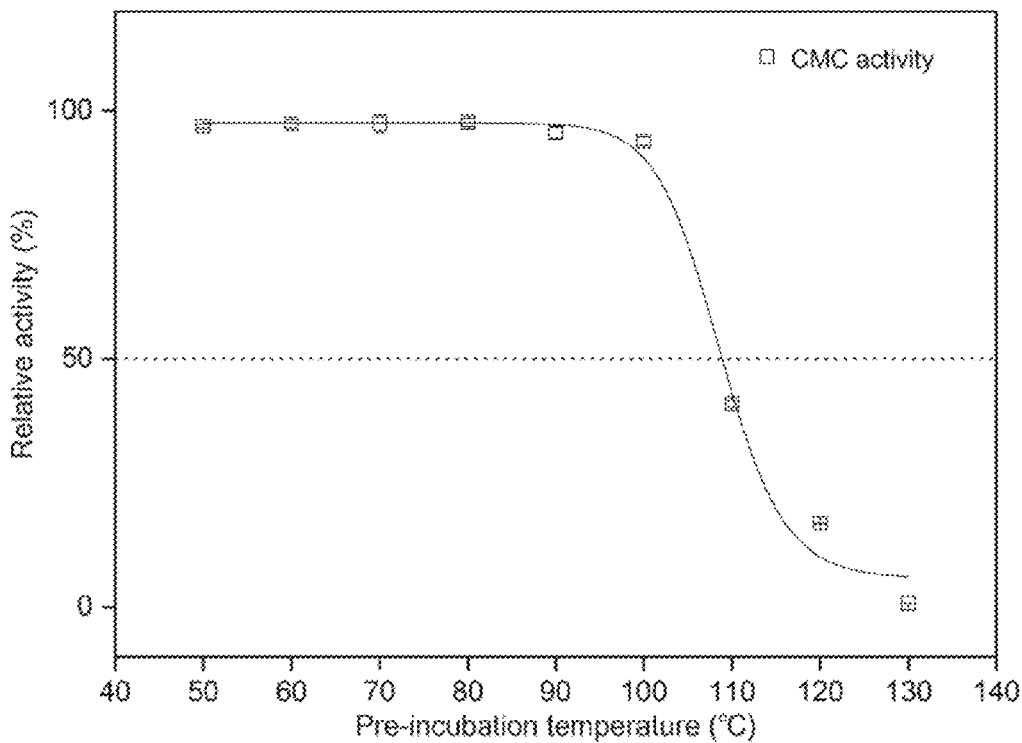
FIG. 8 is a diagram showing the measurement results of the CMC hydrolysis activity (relative value (Relative activity, %) assuming that the activity of the nontreated lot (without preincubation) was 100%) of the AR15G-90-3 protein expressed in *E. coli* in Example 1.
Figure 9:
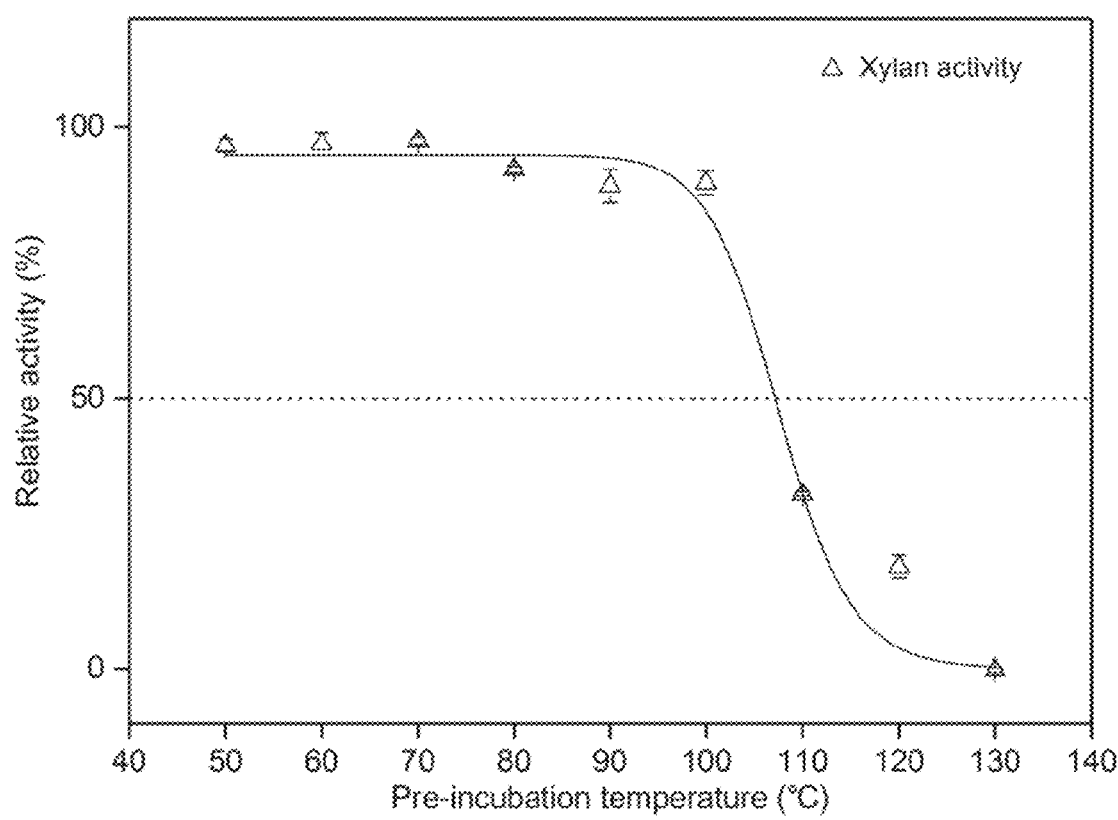
FIG. 9 is a diagram showing the measurement results of the xylanase activity (relative value (%) assuming that the activity of the nontreated lot (without preincubation) was 100%) of the AR15G-90-3 protein expressed in *E. coli* in Example 1.

The measurement results of the CMC hydrolysis activity and the measurement results of the xylan hydrolysis activity are shown in FIG. 8 and FIG. 9, respectively. The enzymatic activity was shown as the relative value (Relative activity, %) assuming that the activity of the nontreated lot (without preincubation) was 100%. The CMC degradation activity of AR15G-90-3 had a $T_{50}$ of 108.6° C., and the xylan degradation activity thereof had a $T_{50}$ of 107.6° C.

Example 2

Based on the whole genome sequence data set of the hot spring soil sample AR15, the assembling was performed once again using the updated assembly software to make an attempt to obtain the full-length sequence of AR15G-90.

<1> Re-assembling of Hot Spring Metagenomic Data

The nucleotide sequence read by the 454 sequencer in Example 1 <1> was assembled with use of the assembly software, Newbler version 2.7 of 454 Life Sciences. The same settings as those in Example 1 <2> were adopted.

<2> Prediction of ORFs of Endoglucanase

Open reading frames (ORF's) were predicted from the contig sequences obtained from the above-mentioned process <2> in the same manner as in Example 1 <3>, with the exception that the Metagene (Noguchi et al., DNA Research, 2008, 15(6)) was used as annotation software.

<3> Open Reading Frame AR15G-90B

The classification of genes into glycoside hydrolase (GH) families was conducted in the same manner as in Example 1 <4>, and an open reading frame (ORF AR15G-90B) which was longer than AR15G-90 by having 55 amino acid residues on the N-end side was obtained by the homology search with BLASTP and HMMER. The open reading frame AR15G-90B encoded a polypeptide including 338 amino acid residues and was a full-length sequence (SEQ ID NO: 9), such that the amino acid residue at position 1 in the polypeptide was methionine (M), and the 3' end of the nucleotide sequence encoding the polypeptide ended with a termination codon. In the above polypeptide, from the amino acid residue at position 56 which was valine (V), the subsequent sequence was the same as that of AR15G-90. According to the analysis using the signal sequence prediction software SignalP 4.1, no signal peptide was predicted. The already known amino acid sequence which showed the highest sequence identity with the amino acid sequence of the polypeptide encoded by the above ORF was that of a glycoside hydrolase family 12 (Genbank: ADM27292.1) of *Ignisphaera aggregans* DSM17230 in the phylum Crenarchaeota. Since the homology between the two amino acid sequences that was calculated by the ClustalW algorithm was 55% for the total length, the aforementioned ORF was verified as a novel sequence.

FIG. 10 shows an alignment of the amino acid sequence (SEQ ID NO: 9) of the polypeptide (AR15G-90B) encoded by the open reading frame AR15G-90B, the amino acid sequence (SEQ ID NO: 1) of the polypeptide (AR15G-90) encoded by the open reading frame AR15G-90, and the amino acid sequence (SEQ ID NO: 8) of a glycoside hydrolase family 12 of *Ignisphaera aggregans* DSM17230. In FIG. 10, the black/white inverted amino acids denote the same amino acid residues (identical) throughout all of these amino acid sequences, and the symbols "-" denote deletions (gaps).

<4> Gene Cloning from Open Reading Frame AR15G-90B

Gene cloning was conducted in the same manner as in Example 1 <6>, with the exception that a forward primer composed of the nucleotide sequence represented by SEQ ID NO: 14 (5'-CACCATGAGTAGAAAGACAGCTGTT-TACATAGCTATAGC-3': obtained by adding 4 nucleotides (CACC) to the 5'-end side of the nucleotide sequence represented by SEQ ID NO: 13. The nucleotides CACC added on the 5' side is a sequence for insertion into a vector) was used.

A gene clone AR15G-90B-15 was obtained from the open reading frame AR15G-90B by PCR cloning. The nucleotide sequence of the endoglucanase candidate gene AR15G-90B-

15 (SEQ ID NO: 12) contained 1,017 bp like that of the open reading frame AR15G-90B (SEQ ID NO: 10), and was different from that of the ORF by 13 nucleotides (Table 2). Of these, differences in nucleotides at three locations also resulted in different amino acids, and the amino acid sequence of the open reading frame AR15G-90B (SEQ ID NO: 9) and the amino acid sequence of the endoglucanase candidate gene AR15G-90B-15 (SEQ ID NO: 11) were different by 3 amino acid residues. That is, the amino acid residue at position 122 was serine (S) in the open reading frame AR15G-90B, whereas it was asparagine (N) in the cloned AR15G-90B-15 gene; the amino acid residue at position 273 was valine (V) in the open reading frame AR15G-90B, whereas it was isoleucine (I) in the cloned AR15G-90B-15 gene; and the amino acid residue at position 314 was methionine (M) in the open reading frame AR15G-90B, whereas it was threonine (T) in the cloned AR15G-90B-15 gene.

TABLE 2

| Nucleotide No. | AR15G-90B | AR15G-90B-15 |
| --- | --- | --- |
| 42 | A | G |
| 126 | A | T |
| 192 | T | A |
| 258 | T | C |
| 365 | G | A |
| 438 | G | T |
| 571 | C | T |
| 630 | A | G |
| 816 | G | A |
| 867 | G | A |
| 871 | C | T |
| 885 | C | T |
| 941 | T | C |

<5> Gene Expression and CMC Hydrolysis Activity Measurement of AR15G-90B-15

Figure 11:
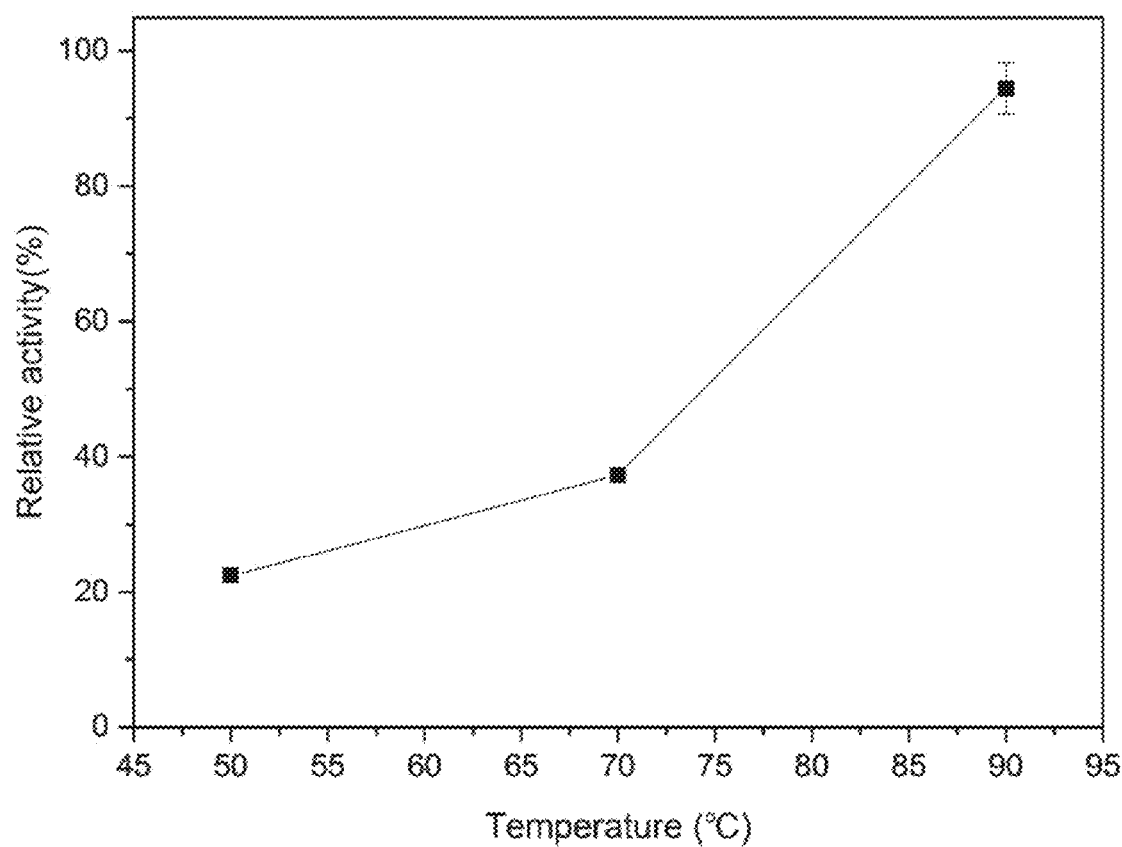
FIG. 11 is a diagram showing the results of the CMC hydrolysis activity (relative value (%) assuming that the activity at a temperature of 90° C. was 100%) of the AR15G-90B-15 protein expressed in *E. coli* measured at respective temperatures in Example 2.

The gene was expressed using *E. coli* in the same manner as in Example 1 <7> and <8>, and the endoglucanase activity of the enzymatic protein (AR15G-90B-15) encoded by the AR15G-90B-15 gene was investigated. The measurement of the CMC hydrolysis activity was conducted by allowing the reaction to proceed for 1 hour at a temperature of 50, 70, or 90° C., using the gene recombinant *E. coli* homogenate supernatant. The measurement was performed by three independent experiments, from which the mean value and the standard errors were obtained. The highest value of the amount of reduced sugar was set to 100%, and the amount of reduced sugar produced by the CMC hydrolysis (pH4.0) by the AR15G-90B-15 protein at respective temperatures was defined as the relative value (%), and was plotted as a relative value of the CMC hydrolysis activity (FIG. 11). AR15G-90B-15 exhibited CMC hydrolysis activity at each temperature, and the temperature at which the highest activity was shown at three measuring points was 90° C.

[Sequence Listing]

What is claimed is:

1. An isolated recombinant hyperthermostable endoglucanase comprising:
a polypeptide comprising an amino acid sequence represented by SEQ ID NO: 3 or SEQ ID NO: 11; and
at least one region selected from the group consisting of a cellulose-binding module, a linker domain, a signal peptide and a tag.

2. An isolated recombinant polynucleotide comprising:
a nucleotide sequence that encodes a polypeptide comprising an amino acid sequence represented by SEQ ID NO: 3 or SEQ ID NO: 11; and
a region which encodes at least one region selected from the group consisting of a cellulose-binding module, a linker domain, a signal peptide and a tag.

3. An expression vector, which is incorporated with the polynucleotide according to claim 2, and which is able to express a polypeptide having endoglucanase activity in a host cell.

4. A transformant, which is introduced with the expression vector according to claim 3.

5. The transformant according to claim 4, which is a eukaryotic microbe.

6. A method for producing a hyperthermostable endoglucanase, the method comprising producing a hyperthermostable endoglucanase in the transformant according to claim 4.

7. A glycoside hydrolase mixture, comprising the hyperthermostable endoglucanase according to claim 1 and at least one or more types of other glycoside hydrolases.

8. A glycoside hydrolase mixture, comprising a hyperthermostable endoglucanase encoded by the polynucleotide according to claim 2 and at least one or more types of other glycoside hydrolases.

9. A glycoside hydrolase mixture, comprising a hyperthermostable endoglucanase produced by the method for producing a hyperthermostable endoglucanase according to claim 6 and at least one or more types of other glycoside hydrolases.

10. A method for producing a lignocellulose degradation product, the method comprising producing a lignocellulose degradation product by bringing a material composed of lignocellulose comprising cellulose into contact with the hyperthermostable endoglucanase according to claim 1.

11. A method for producing a lignocellulose degradation product, the method comprising producing a lignocellulose degradation product by bringing a material composed of lignocellulose comprising cellulose into contact with a hyperthermostable endoglucanase encoded by the polynucleotide according to claim 2.

12. A method for producing a lignocellulose degradation product, the method comprising producing a lignocellulose degradation product by bringing a material composed of lignocellulose comprising cellulose into contact with the transformant according to claim 4.

13. A method for producing a lignocellulose degradation product, the method comprising producing a lignocellulose degradation product by bringing a material composed of lignocellulose comprising cellulose into contact with a hyperthermostable endoglucanase produced by the method for producing a hyperthermostable endoglucanase according to claim 6.

14. A method for producing a lignocellulose degradation product, the method comprising producing a lignocellulose degradation product by bringing a material composed of lignocellulose comprising cellulose into contact with the glycoside hydrolase mixture according to claim 7.

15. A method for producing a lignocellulose degradation product, the method comprising producing a lignocellulose degradation product by bringing a material composed of lignocellulose comprising cellulose into contact with the glycoside hydrolase mixture according to claim 8.

16. A method for producing a lignocellulose degradation product, the method comprising producing a lignocellulose degradation product by bringing a material composed of lignocellulose comprising cellulose into contact with the glycoside hydrolase mixture according to claim 9.

* * * * *

SEQUENCE LISTING

```
<160> NUMBER OF SEQ ID NOS: 14

<210> SEQ ID NO 1
<211> LENGTH: 283
<212> TYPE: PRT
<213> ORGANISM: Unknown
<220> FEATURE:
<223> OTHER INFORMATION: Deduced amino acid sequence of open reading
      frame AR15G-90

<400> SEQUENCE: 1

Val Thr Ile Thr Pro Ser Thr Thr Pro Gln Gln Leu Arg Ala Ile Thr
1               5                   10                  15

Leu Arg Tyr Pro Gly Asn Ser Ser Ser Pro Val Asp Leu Asn Ser Asp
            20                  25                  30

Gly Val Tyr Asp Val Leu Leu Glu Ile Asn Pro Trp Asn Met Glu Lys
        35                  40                  45

Ala Asp Gly Phe Gln Thr Ile Val Val Asp Leu Ile Asn Gly Val Ile
    50                  55                  60

Lys Val Ser Ser Asp Leu Ala Asn Val Tyr Pro Pro Asn Trp Ala Asn
65                  70                  75                  80

Gly Tyr Pro Glu Ile Ile Ile Gly Arg Lys Pro Trp Thr Thr Tyr Tyr
                85                  90                  95

Tyr Asn Gly Leu Gly Val Glu Phe Pro Met Arg Val Arg Asp Ala Arg
            100                 105                 110

Pro Phe Val Ile Ser Phe Tyr Ile Cys Val Glu His Leu Asp Pro Ser
```

```
              115                 120                 125
Met Asn Phe Asn Ile Ala Ala Asp Ala Trp Ile Val Arg Glu Ser Ile
130                 135                 140

Ala Met Ser Leu Gly Met Pro Pro Ala Lys Gly Asp Leu Glu Ile Met
145                 150                 155                 160

Val Trp Leu Phe Ser Gln Asn Leu Asn Pro Ala Gly Arg Lys Ile Gly
                165                 170                 175

Glu Glu Val Val Pro Ile Ser Ile Asn Gly Ser Val Ile Glu Ala Val
            180                 185                 190

Phe Glu Val Trp Arg His Asp Ser Val Glu Trp Gly Gly Trp Gln Tyr
        195                 200                 205

Ile Ala Phe Arg Pro Lys Met Trp Gly Val Arg Cys Gly Tyr Ile Ala
210                 215                 220

Tyr Asn Pro Ile Asp Phe Val Thr Ala Ala Ser Lys Tyr Ala Thr Phe
225                 230                 235                 240

Asp Ile Ser Asp Tyr Tyr Leu Leu Gly Trp Glu Ile Gly Thr Glu Trp
                245                 250                 255

Gly Thr Met Thr Ser Asn Gly Leu Ala Lys Phe Ser Trp Phe Leu Lys
            260                 265                 270

Asp Leu Glu Ile Gln Pro Gly Lys Thr Leu Arg
        275                 280

<210> SEQ ID NO 2
<211> LENGTH: 852
<212> TYPE: DNA
<213> ORGANISM: Unknown
<220> FEATURE:
<223> OTHER INFORMATION: Open reading frame AR15G-90

<400> SEQUENCE: 2
gtgaccatca cgccgagtac aacacctcaa cagctcagag ctataacctt gagatacccc      60
ggcaactctt cttcgcctgt agatctcaac agtgatggtg tttacgatgt tcttttagag     120
ataaacccgt ggaatatgga gaaagccgac ggatttcaga caatagttgt agacctaatt     180
aacggtgtta ttaaggtgag ctctgatcta gccaatgtat acccaccgaa ctgggctaat     240
ggctaccctg agataatcat cggtagaaag ccgtggacta cgtactacta caacggctta     300
ggcgtagaat tcctatgag agtacgcgac gctagaccct ttgtaatctc gttctatata     360
tgcgtagagc acctagaccc atcgatgaac ttcaacatag cggctgacgc ctggattgtt     420
agagaaagca ttgcgatgag cttgggtatg ccgcctgcta aggagatct agagataatg     480
gtgtggctct tcagccaaaa ccttaaccca gctggtagga aaatcgggga ggaagtagta     540
cccatatcta tcaacgggag tgttatagaa gctgttttcg aggtctggag acatgatagc     600
gttgagtggg gtgggtggca gtatatagcg tttaggccta gatgtggggg ggttaggtgc     660
ggctatatag cgtacaaccc tatagacttc gtgactgcgg cgtctaagta cgctacattc     720
gatatatctg actactacct cttaggctgg gagatatggga ctgagtgggg cactatgaca     780
tctaatggtc tggctaagtt ctcgtggttt ttgaaagatc tcgagattca gccaggtaaa     840
acactgaggt ag                                                        852

<210> SEQ ID NO 3
<211> LENGTH: 283
<212> TYPE: PRT
<213> ORGANISM: Unknown
<220> FEATURE:
<223> OTHER INFORMATION: Amino acid sequence of AR15G-90-3
```

<400> SEQUENCE: 3

```
Val Thr Ile Thr Pro Ser Thr Thr Pro Gln Gln Leu Arg Ala Ile Thr
1               5                   10                  15

Leu Arg Tyr Pro Gly Asn Ser Ser Pro Val Asp Leu Asn Ser Asp
            20                  25                  30

Gly Val Tyr Asp Val Leu Leu Glu Ile Asn Pro Trp Asn Met Glu Lys
                35                  40                  45

Ala Asp Gly Phe Gln Thr Ile Val Val Asp Leu Ile Asn Gly Val Ile
        50                  55                  60

Lys Val Ser Ser Asp Leu Ala Asn Val Tyr Pro Pro Asn Trp Ala Asn
65                  70                  75                  80

Gly Tyr Pro Glu Ile Ile Gly Arg Lys Pro Trp Thr Thr Tyr Tyr
                85                  90                  95

Tyr Asn Gly Leu Gly Val Glu Phe Pro Met Arg Val Arg Asp Ala Lys
            100                 105                 110

Pro Phe Val Ile Ser Phe Tyr Ile Cys Val Glu His Leu Asp Pro Ser
            115                 120                 125

Met Asn Phe Asn Ile Ala Ala Asp Ala Trp Ile Val Arg Glu Ser Ile
130                 135                 140

Ala Met Ser Leu Gly Met Pro Pro Ala Lys Gly Asp Leu Glu Ile Met
145                 150                 155                 160

Val Trp Leu Phe Ser Gln Asn Leu Asn Pro Ala Gly Arg Lys Ile Gly
                165                 170                 175

Glu Glu Val Val Pro Ile Ser Ile Asn Gly Ser Val Ile Glu Ala Val
            180                 185                 190

Phe Glu Val Trp Arg His Asp Ser Val Glu Trp Gly Trp Gln Tyr
            195                 200                 205

Ile Ala Phe Arg Pro Lys Met Trp Gly Ile Arg Cys Gly Tyr Ile Ala
        210                 215                 220

Tyr Asn Pro Ile Asp Phe Val Thr Ala Ala Ser Lys Tyr Ala Thr Phe
225                 230                 235                 240

Asp Ile Ser Asp Tyr Tyr Leu Leu Gly Trp Glu Ile Gly Thr Glu Trp
            245                 250                 255

Gly Thr Met Thr Ser Asn Gly Leu Ala Lys Phe Ser Trp Phe Leu Lys
            260                 265                 270

Asp Leu Glu Ile Gln Pro Gly Lys Thr Leu Arg
            275                 280
```

<210> SEQ ID NO 4
<211> LENGTH: 852
<212> TYPE: DNA
<213> ORGANISM: Unknown
<220> FEATURE:
<223> OTHER INFORMATION: Nucleotide sequence encoding the amino acid sequence of AR15G-90-3

<400> SEQUENCE: 4

```
gtgaccatca cgccgagtac aacacctcaa cagctcagag ctataacctt gagataccccc      60 ggcaactctt cttcgcctgt agatctcaac agcgatggtg tttacgatgt tcttttagag     120
ataaacccgt ggaatatgga aaagccgac ggatttcaga caatagttgt agacctaatt     180
aacggtgtta ttaaggtgag ctctgatcta gccaatgtat acccaccgaa ctgggctaat     240
ggctaccctg agataatcat cggtagaaag ccgtggacta cgtactacta caacggctta     300
ggcgtagaat tcctatgag agtacgcgac gctaaacctt ttgtaatctc gttctatata     360
```

```
tgcgtagagc acctagaccc atcgatgaac ttcaacatag cggctgacgc ctggattgtt      420
agagaaagca ttgcgatgag cttgggtatg ccgcctgcta aaggagatct agagataatg      480
gtgtggctct tcagccaaaa ccttaaccca gctggtagga aaatcgggga ggaagtagta      540
cccatatcta tcaacgggag tgttatagaa gctgttttcg aggtctggag acatgatagc      600
gttgagtggg gtgggtggca gtatatagcg tttaggccta agatgtgggg gattaggtgc      660
ggctatatag cgtacaaccc tatagacttc gtgactgcag cgtctaagta cgctacattc      720
gatatatctg actactacct cttaggctgg gagataggga ctgagtgggg cactatgaca      780
tctaatggtc tggctaagtt ctcgtggttt ttgaaagatc tcgagattca gccaggtaaa      840
acactgaggt ag                                                         852
```

```
<210> SEQ ID NO 5
<211> LENGTH: 21
<212> TYPE: DNA
<213> ORGANISM: Artificial Sequence
<220> FEATURE:
<223> OTHER INFORMATION: Primer; nucleotide sequence which is homologous
      (identical) with a partial sequence including the nucleotides at
      position 1 to 21 of the nucleotide sequence represented by SEQ ID
      NO: 2

<400> SEQUENCE: 5
gtgaccatca cgccgagtac a                                                21

<210> SEQ ID NO 6
<211> LENGTH: 22
<212> TYPE: DNA
<213> ORGANISM: Artificial Sequence
<220> FEATURE:
<223> OTHER INFORMATION: Primer; nucleotide sequence which is
      complementary with a partial sequence including the nucleotides at
      position 831 to 852 of the nucleotide sequence represented by SEQ
      ID NO: 2

<400> SEQUENCE: 6
ctacctcagt gttttacctg gc                                               22

<210> SEQ ID NO 7
<211> LENGTH: 28
<212> TYPE: DNA
<213> ORGANISM: Artificial Sequence
<220> FEATURE:
<223> OTHER INFORMATION: Forward primer

<400> SEQUENCE: 7
caccatggtg accatcacgc cgagtaca                                         28

<210> SEQ ID NO 8
<211> LENGTH: 388
<212> TYPE: PRT
<213> ORGANISM: Unknown
<220> FEATURE:
<223> OTHER INFORMATION: Amino acid sequence of a glycoside hydrolase
      family 12 of Ignisphaera aggregans DSM17230

<400> SEQUENCE: 8
```

Met Ala Val Ser Gly Leu Gln Ile Ile Val Val Ile Leu Val Ile Ala
1               5                   10                  15

Leu Leu Ala Leu Gly Ile Tyr Ile Val Ile Gly Gly Pro Gly Thr Lys
            20                  25                  30

Thr Ile Val Thr Glu Thr Ile Thr Tyr Thr Glu Thr Val Pro Arg Thr

```
            35                  40                  45
Ile Ile Gln Gln Glu Thr Lys Thr Ile Thr Thr Ile Pro Thr Thr
 50                  55                  60

Ile Glu Gly Ile Val Arg Glu Thr Thr Thr Glu Thr Gln Tyr Thr Thr
 65                  70                  75                  80

Val Thr Ser Ile Ala Thr Val Thr Met Thr Ser Ile Leu Thr Ser Thr
                 85                  90                  95

Val Tyr Gln Thr Val Ser Gln Thr Ile Tyr Thr Thr Thr Ile Thr
                100                 105                 110

Ser Pro Met Ser Ile Ile Leu Glu Tyr Pro Lys Asp Leu Ser Thr Val
                115                 120                 125

Lys Thr Leu Asp Ile Asn Gly Asp Gly Ile Ser Asp Val Lys Val Ala
                130                 135                 140

Ile Asn Pro Trp Asn Met Arg Ser Ala Gln Gly Tyr Gln Lys Met Ile
145                 150                 155                 160

Ile Asn Leu Ser Thr Arg Ser Ile Lys Phe Ile Ser Asn Leu Thr Asn
                165                 170                 175

Val Ser Pro Ala Glu Trp Thr Asn Gly Tyr Pro Glu Ile Tyr Ile Gly
                180                 185                 190

Arg Lys Pro Trp Asp Tyr Ser Tyr Val Asn Gly Phe Gly Val Ala Phe
                195                 200                 205

Pro Met Lys Ile Ser Glu Leu Lys Pro Phe Val Val Ser Phe Tyr Ile
210                 215                 220

Cys Ile Asp Arg Leu Asp Pro Ser Met Asn Phe Asn Ile Ala Ala Asp
225                 230                 235                 240

Ala Trp Ile Val Arg Glu Ser Ile Ala Arg Asn Ala Gly Ala Ser Pro
                245                 250                 255

Ser Gln Gly Asp Ile Glu Ile Met Val Trp Leu Phe Asn Gln Asn Leu
                260                 265                 270

Gln Pro Ala Gly Ser Arg Ile Gly Glu Glu Ile Leu Pro Ile Val Ile
                275                 280                 285

Asn Gly Thr Lys Tyr Tyr Lys Thr Phe Glu Val Trp Lys Met Asn Ser
290                 295                 300

Val Pro Trp Gly Gly Trp Asp Tyr Ile Ala Phe Lys Pro Lys Asp Trp
305                 310                 315                 320

Ser Ile Arg Cys Gly Ser Val Val Tyr Asp Pro Thr Gln Phe Val Lys
                325                 330                 335

Ala Leu Ser Lys Tyr Thr Asp Gly Ile Asp Ile Ser Asn Tyr Tyr Leu
                340                 345                 350

Leu Asp Trp Glu Ile Gly Thr Glu Trp Gly Ser Arg Thr Ser Asn Gly
                355                 360                 365

Ile Ala Ile Phe Glu Trp Thr Ile Arg Asp Phe Met Ala Ile Pro Gly
                370                 375                 380

Ile Glu Ile Lys
385

<210> SEQ ID NO 9
<211> LENGTH: 338
<212> TYPE: PRT
<213> ORGANISM: Unknown
<220> FEATURE:
<223> OTHER INFORMATION: Deduced amino acid sequence of open reading
      frame AR15G-90B

<400> SEQUENCE: 9
```

Met Ser Arg Lys Thr Ala Val Tyr Ile Ala Ile Ala Leu Leu Thr Leu
1               5                   10                  15

Val Ile Gly Phe Leu Ala Gly Tyr Gln Tyr Gly Val Ser Arg Val Glu
            20                  25                  30

Thr Val Thr Thr Thr Val Thr Thr Thr Ala Thr Thr Thr Phe Tyr Ser
        35                  40                  45

Thr Thr Thr Ile Thr Thr Thr Val Thr Ile Thr Pro Ser Thr Thr Pro
    50                  55                  60

Gln Gln Leu Arg Ala Ile Thr Leu Arg Tyr Pro Gly Asn Ser Ser Ser
65                  70                  75                  80

Pro Val Asp Leu Asn Ser Asp Gly Val Tyr Asp Val Leu Leu Glu Ile
                85                  90                  95

Asn Pro Trp Asn Met Glu Lys Ala Asp Gly Phe Gln Thr Ile Val Val
            100                 105                 110

Asp Leu Ile Asn Gly Val Ile Lys Val Ser Ser Asp Leu Ala Asn Val
        115                 120                 125

Tyr Pro Pro Asn Trp Ala Asn Gly Tyr Pro Glu Ile Ile Ile Gly Arg
    130                 135                 140

Lys Pro Trp Thr Thr Tyr Tyr Tyr Asn Gly Leu Gly Val Glu Phe Pro
145                 150                 155                 160

Met Arg Val Arg Asp Ala Arg Pro Phe Val Ile Ser Phe Tyr Ile Cys
                165                 170                 175

Val Glu His Leu Asp Pro Ser Met Asn Phe Asn Ile Ala Ala Asp Ala
            180                 185                 190

Trp Ile Val Arg Glu Ser Ile Ala Met Ser Leu Gly Met Pro Pro Ala
        195                 200                 205

Lys Gly Asp Leu Glu Ile Met Val Trp Leu Phe Ser Gln Asn Leu Asn
210                 215                 220

Pro Ala Gly Arg Lys Ile Gly Glu Glu Val Val Pro Ile Ser Ile Asn
225                 230                 235                 240

Gly Ser Val Ile Glu Ala Val Phe Glu Val Trp Arg His Asp Ser Val
                245                 250                 255

Glu Trp Gly Gly Trp Gln Tyr Ile Ala Phe Arg Pro Lys Met Trp Gly
            260                 265                 270

Val Arg Cys Gly Tyr Ile Ala Tyr Asn Pro Ile Asp Phe Val Thr Ala
        275                 280                 285

Ala Ser Lys Tyr Ala Thr Phe Asp Ile Ser Asp Tyr Tyr Leu Leu Gly
    290                 295                 300

Trp Glu Ile Gly Thr Glu Trp Gly Thr Met Thr Ser Asn Gly Leu Ala
305                 310                 315                 320

Lys Phe Ser Trp Phe Leu Lys Asp Leu Glu Ile Gln Pro Gly Lys Thr
                325                 330                 335

Leu Arg

<210> SEQ ID NO 10
<211> LENGTH: 1017
<212> TYPE: DNA
<213> ORGANISM: Unknown
<220> FEATURE:
<223> OTHER INFORMATION: Open reading frame AR15G-90B

<400> SEQUENCE: 10
atgagtagaa agacagctgt ttacatagct atagctctgc taacccttgt aataggcttt     60
ctagcaggtt accagtacgg tgttagcaga gtagagactg taaccacaac tgttacaaca    120

```
actgcaacca caacgtttta tagcactaca actataacca ctactgtgac catcacgccg    180
agtacaacac ctcaacagct cagagctata accttgagat accccggcaa ctcttcttcg    240
cctgtagatc tcaacagtga tggtgtttac gatgttcttt agagataaa cccgtggaat     300 atggagaaag ccgacggatt tcagacaata gttgtagacc taattaacgg tgttattaag    360
gtgagctctg atctagccaa tgtatacccca ccgaactggg ctaatggcta ccctgagata   420
atcatcggta gaaagccgtg gactacgtac tactacaacg gcttaggcgt agaatttcct    480
atgagagtac gcgacgctag acctttgta atctcgttct atatatgcgt agagcaccta    540
gacccatcga tgaacttcaa catagcggct gacgcctgga ttgttagaga aagcattgcg    600
atgagcttgg gtatgccgcc tgctaaagga gatctagaga taatggtgtg gctcttcagc    660 caaaaccta acccagctgg taggaaaatc ggggaggaag tagtacccat atctatcaac     720
gggagtgtta tagaagctgt tttcgaggtc tggagacatg atagcgttga gtggggtggg    780
tggcagtata tagcgtttag gcctaagatg tggggggtta ggtgcggcta tatagcgtac    840
aaccctatag acttcgtgac tgcggcgtct aagtacgcta cattcgatat atctgactac    900
tacctcttag gctgggagat agggactgag tggggcacta tgacatctaa tggtctggct    960
aagttctcgt ggttttttgaa agatctcgag attcagccag gtaaaacact gaggtag    1017
```

<210> SEQ ID NO 11
<211> LENGTH: 338
<212> TYPE: PRT
<213> ORGANISM: Unknown
<220> FEATURE:
<223> OTHER INFORMATION: Amino acid sequence of the endoglucanase
      candidate gene AR15G-90B-15

<400> SEQUENCE: 11

```
Met Ser Arg Lys Thr Ala Val Tyr Ile Ala Ile Ala Leu Leu Thr Leu
1               5                   10                  15

Val Ile Gly Phe Leu Ala Gly Tyr Gln Tyr Gly Val Ser Arg Val Glu
            20                  25                  30

Thr Val Thr Thr Thr Val Thr Thr Thr Ala Thr Thr Thr Phe Tyr Ser
        35                  40                  45

Thr Thr Thr Ile Thr Thr Thr Val Thr Ile Thr Pro Ser Thr Thr Pro
    50                  55                  60

Gln Gln Leu Arg Ala Ile Thr Leu Arg Tyr Pro Gly Asn Ser Ser Ser
65                  70                  75                  80

Pro Val Asp Leu Asn Ser Asp Gly Val Tyr Asp Val Leu Leu Glu Ile
                85                  90                  95

Asn Pro Trp Asn Met Glu Lys Ala Asp Gly Phe Gln Thr Ile Val Val
            100                 105                 110

Asp Leu Ile Asn Gly Val Ile Lys Val Asn Ser Asp Leu Ala Asn Val
        115                 120                 125

Tyr Pro Pro Asn Trp Ala Asn Gly Tyr Pro Glu Ile Ile Gly Arg
    130                 135                 140

Lys Pro Trp Thr Thr Tyr Tyr Tyr Asn Gly Leu Gly Val Glu Phe Pro
145                 150                 155                 160

Met Arg Val Arg Asp Ala Arg Pro Phe Val Ile Ser Phe Tyr Ile Cys
                165                 170                 175

Val Glu His Leu Asp Pro Ser Met Asn Phe Asn Ile Ala Ala Asp Ala
            180                 185                 190

Trp Ile Val Arg Glu Ser Ile Ala Met Ser Leu Gly Met Pro Pro Ala
        195                 200                 205
```

```
Lys Gly Asp Leu Glu Ile Met Val Trp Leu Phe Ser Gln Asn Leu Asn
            210                 215                 220

Pro Ala Gly Arg Lys Ile Gly Glu Glu Val Val Pro Ile Ser Ile Asn
225                 230                 235                 240

Gly Ser Val Ile Glu Ala Val Phe Glu Val Trp Arg His Asp Ser Val
                245                 250                 255

Glu Trp Gly Gly Trp Gln Tyr Ile Ala Phe Arg Pro Lys Met Trp Gly
            260                 265                 270

Ile Arg Cys Gly Tyr Ile Ala Tyr Asn Pro Ile Asp Phe Val Thr Ala
        275                 280                 285

Ala Ser Lys Tyr Ala Thr Phe Asp Ile Ser Asp Tyr Tyr Leu Leu Gly
    290                 295                 300

Trp Glu Ile Gly Thr Glu Trp Gly Thr Thr Thr Ser Asn Gly Leu Ala
305                 310                 315                 320

Lys Phe Ser Trp Phe Leu Lys Asp Leu Glu Ile Gln Pro Gly Lys Thr
                325                 330                 335

Leu Arg

<210> SEQ ID NO 12
<211> LENGTH: 1017
<212> TYPE: DNA
<213> ORGANISM: Unknown
<220> FEATURE:
<223> OTHER INFORMATION: Nucleotide sequence of the endoglucanase
      candidate gene AR15G-90B-15

<400> SEQUENCE: 12
atgagtagaa agacagctgt ttacatagct atagctctgc tgacccttgt aataggcttt      60
ctagcaggtt accagtacgg tgttagcaga gtagagactg taaccacaac tgttacaaca     120
actgctacca caacgtttta tagcactaca actataacca ctactgtgac catcacgccg     180
agtacaacac cacaacagct cagagctata accttgagat accccggcaa ctcttcttcg     240
cctgtagatc tcaacagcga tggtgtttac gatgttcttt tagagataaa cccgtggaat     300
atggagaaag ccgacggatt tcagacaata gttgtagacc taattaacgg tgttattaag     360
gtgaactctg atctagccaa tgtatacccca ccgaactggg ctaatggcta ccctgagata     420
atcatcggta gaaagccttg gactacgtac tactacaacg gcttaggcgt agaatttcct     480
atgagagtac gcgacgctag accttttgta atctcgttct atatatgcgt agagcaccta     540
gacccatcga tgaacttcaa tatagcggct gacgcctgga ttgttagaga aagcattgcg     600
atgagcttgg gtatgccgcc tgctaaaggg gatctagaga taatggtgtg gctcttcagc     660
caaaacctta acccagctgg taggaaaatc ggggaggaag tagtacccat atctatcaac     720
gggagtgtta tagaagctgt tttcgaggtc tggagacatg atagcgttga gtggggtggg     780
tggcagtata tagcgtttag gcctaagatg tgggggatta ggtgcggcta tatagcgtac     840
aaccctatag acttcgtgac tgcggcatct aagtatgcta catttgatat atctgactac     900
tacctcttag gctgggagat agggactgag tggggcacta cgacatctaa tggtctggct     960
aagttctcgt ggtttttgaa agatctcgag attcagccag gtaaaacact gaggtag      1017

<210> SEQ ID NO 13
<211> LENGTH: 35
<212> TYPE: DNA
<213> ORGANISM: Artificial Sequence
<220> FEATURE:
<223> OTHER INFORMATION: Primer
```

```
<400> SEQUENCE: 13
atgagtagaa agacagctgt ttacatagct atagc                              35

<210> SEQ ID NO 14
<211> LENGTH: 39
<212> TYPE: DNA
<213> ORGANISM: Artificial Sequence
<220> FEATURE:
<223> OTHER INFORMATION: Primer; obtained by adding 4 nucleotides (CACC)
      to the 5'-end side of the nucleotide sequence represented by SEQ
      ID NO: 13

<400> SEQUENCE: 14
caccatgagt agaaagacag ctgtttacat agctatagc                          39
```